US010620200B2

(12) United States Patent
Li et al.

(10) Patent No.: US 10,620,200 B2
(45) Date of Patent: Apr. 14, 2020

(54) METHODS AND COMPOSITIONS FOR HYBRID MICROFLUIDIC DEVICES INTEGRATED WITH NANO-BIOSENSORS

(71) Applicants:XiuJun Li, El Paso, TX (US); Maowei Dou, El Paso, TX (US)

(72) Inventors: XiuJun Li, El Paso, TX (US); Maowei Dou, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 738 days.

(21) Appl. No.: 14/725,689

(22) Filed: May 29, 2015

(65) Prior Publication Data

US 2015/0346199 A1 Dec. 3, 2015

Related U.S. Application Data

(60) Provisional application No. 62/004,260, filed on May 29, 2014.

(51) Int. Cl.
| | |
|---|---|
| *G01N 33/543* | (2006.01) |
| *C40B 60/10* | (2006.01) |
| *G01N 33/569* | (2006.01) |
| *B01L 3/00* | (2006.01) |
| *C12Q 1/689* | (2018.01) |

(52) U.S. Cl.
CPC ...... *G01N 33/54386* (2013.01); *B01L 3/5023* (2013.01); *B01L 3/5027* (2013.01); *C12Q 1/689* (2013.01); *G01N 33/56911* (2013.01); *B01L 2200/10* (2013.01); *B01L 2300/069* (2013.01); *B01L 2300/0636* (2013.01); *B01L 2300/0681* (2013.01); *B01L 2300/0803* (2013.01); *B01L 2300/0864* (2013.01); *B01L 2300/126* (2013.01); *B01L 2400/0409* (2013.01); *G01N 2333/22* (2013.01); *G01N 2333/255* (2013.01); *G01N 2333/31* (2013.01); *G01N 2333/3156* (2013.01); *G01N 2333/335* (2013.01)

(58) Field of Classification Search
CPC ....... G01N 33/543; G01N 33/569; C12Q 1/68
See application file for complete search history.

(56) References Cited

U.S. PATENT DOCUMENTS

| | | | | |
|---|---|---|---|---|
| 5,310,523 A | | 5/1994 | Smethers et al. | 422/404 |
| 7,981,694 B2* | | 7/2011 | Boss | C07K 14/4722 436/518 |
| 8,921,118 B2* | | 12/2014 | Siegel | B01L 3/502707 422/412 |
| 2009/0104077 A1* | | 4/2009 | Momose | B01L 3/50273 422/72 |
| 2009/0281250 A1* | | 11/2009 | DeSimone | B29C 66/9534 525/418 |
| 2010/0021910 A1* | | 1/2010 | Cao | B01L 3/502753 435/6.11 |
| 2012/0181184 A1* | | 7/2012 | Whitesides | B01L 3/502 205/775 |
| 2013/0203634 A1* | | 8/2013 | Jovanovich | B01L 3/502738 506/26 |

OTHER PUBLICATIONS

Nie et al., Integration of Paper-Based Microfluidic Devices with Commercial Electrochemical Readers, Lab on a Chip, 2010, 10, 3163-3169. (Year: 2010).*
Li et al., A PDMS/Paper Hybrid Microfluidic Device Integrated With Graphene Oxide-Based nano-Biosensors for Multiplexed Pathogen Detection, 17th International Conference on Miniaturized Systems for Chemistry and Life Sciences, Oct. 27-31, 2013, Freiburg, Germany, published Jan. 2013, 705-707. (Year: 2013).*
Wang et al., Aptamer-Based Fluorescent Biosensors, NIH Public Access, Author Manuscript, 2011, 1-22. (Year: 2011).*
Li et al. Publication Date, A PDMS/Paper Hybrid Microfluidic Device Integrated with Graphene Oxide-Based Nano-Biosensors for Multiplexed Pathogen Detection, Influuent, 17th International Conference on Miniaturized Systems for Chemistry and Life Sciences (MicroTAS 2013), Jan. 1, 2013, 705-707. (Year: 2013).*
Lu et al., A Graphene Platform for Sensing Biomolecules, Angew. Chem. Int. Ed., 2009, 48, 4785-4787. (Year: 2009).*
Lu et al., A Graphene Platform for Sensing Biomolecules, Angewandte Chemie, 2009, 48, 4785-4787. (Year: 2009).*
Lu et al., Patterned Paper as a Low-Cost, Flexible Substrate for Rapid Prototyping of PDMS Microdevices via "Liquid Molding", Analytical Chemistry, 2011, 83, 1830-1835. (Year: 2011).*
Zhang et al., Fabrication of Paper-Based Microfluidic Device Using Printed Circuit Technology, AIP Advances, 2012, 2, 1-7. (Year: 2012).*
Filtrox, Filter Sheets & Sheet Filters, Filtrox, 2019, 1-4. (Year: 2019).*
Ahmad et al. "A CCD-based fluorescence imaging system for real-time loop-mediated isothermal amplification-based rapid and sensitive detection of waterborne pathogens on microchips", (2011) *Biomed Microdevices*, 13(5): 929-37.
Blackwell et al. "Differences and similarities in DNA-binding preferences of MyoD and E2A protein complexes revealed by binding site selection", *Science* (1990) 250:1104-1110.
Blackwell et al. "Sequence-specific DNA binding by the c-Myc protein", *Science* (1990) 250:1149-1152.
Cao et al., "Combining use of a panel of ssDNA aptamers in the detection of *Staphylococcus aureus*", *Nucleic Acids Res*, 2009, 37:4621-28.
Chang et al. "Graphene fluorescence resonance energy transfer aptasensor for the thrombin detection", *Anal. Chem.* 2010. 82:2341-46.
Edgar et al., 2006, "High-sensitivity bacterial detection using biotin-tagged phage and quantum-dot nanocomplexes", *Proc Natl Acad Sci USA*, 103(13):4841-45.

(Continued)

*Primary Examiner* — Amy M Bunker
(74) *Attorney, Agent, or Firm* — Norton Rose Fulbright US LLP

(57) ABSTRACT

Certain embodiments are directed to paper/polymer hybrid microfluidic devices integrated with nano-biosensors for pathogen detection and infectious disease diagnosis.

11 Claims, 15 Drawing Sheets

Specification includes a Sequence Listing.

(56) References Cited

OTHER PUBLICATIONS

Hamula et al., "Selection of aptamers against live bacterial cells", *Anal Chem.*, 2008, 80:7812-19.

Joshi et al., "Selection, characterization, and application of DNA aptamers for the capture and detection of *Salmonella enterica* serovars", *Mol. Cell Probe*, 2009, 23:20-28.

Joyce "Amplification, mutation and selection of catalytic RNA", *Gene* (1989) 82:83-87.

Kim et al., "The enhanced pneumococcal LAMP assay: a clinical tool for the diagnosis of meningitis due to *Streptococcus pneumoniae*", *PLoS One*, 2012, 7(8):e42954.

Kovarik et al., "Micro total analysis systems for cell biology and biochemical assays", 2011, *Analytical Chemistry*, 84:516-40.

Labroo, et al., Graphene nano-ink biosensor arrays on a microfluidic paper for multiplexed detection of metabolites. Analytica Chimica Acta. 813:90-96, Feb. 27, 2014 [retrieved on Jul. 31, 2015] retrieved from the internet: http://www.sciencedirect.com/science/article/pii/S0003267014000701.

Li and Li, "Strategies for the real-time detection of Ca2+ channel events of single cells: recent advances and new possibilities", 2010, *Expert Review of Clinical Pharmacology*, 3:267-80.

Li, et al., A PDMS/Paper hybrid microfluidic device integrated with graphene oxide-based nano-biosensors for multiplexed pathogen detecttion. 17th International Conference on Miniatureized Systems for Chemistry and Life Sciences. pp. 705-707, 27-31, Oct. 2013 [retrieved on Jul. 30, 2015] Retrieved from the internet http://www.rsc.org/images/loc/2013/PDFs/papers/237_0499.pdf.

Loh et al., "Graphene oxide as a chemically tunable platform for optical applications", 2010, *Nat Chem*, 2(12):1015-24.

McKenna et al., "Development and clinical validation of a loop-mediated isothermal amplification method for the rapid detection of Neisseria meningitides", *Diagnostic Microbiology and Infectious Disease*, 2011, 69(2):137-44.

Mothershed et al., "Use of real-time PCR to resolve slide agglutination discrepancies in serogroup identification of Neisseria meningitides", *Journal of clinical microbiology*, 2004, 42(1):320-8.

Salieb-Beugelaar et al., "Latest developments in microfluidic cell biology and analysis systems", 2010, *Analytical Chemistry*, 82:4848-64.

Search Report and Written Opinion in International Application No. PCT/US2015/033203 dated Aug. 14, 2015.

Smith et al., "Multicolor quantum dots for molecular diagnostics of cancer", 2006, *Expert Rev Mol Diagn*, 6(2):231-44.

Taton et al., "Scanometric DNA array detection with nanoparticle probes", 2000, *Science*, 289(5485): 1757-60.

Tsai et al., "Violet light emitting diode-induced fluorescence detection combined with on-line sample concentration techniques for use in capillary electrophoresis", 2003, *Electrophoresis*, 24(17):3083-88.

Tuerk and Gold "Systematic evolution of ligands by exponential enrichment: RNA ligands to bacteriophage T4 DNA polymerase", *Science* (1990) 249:505-510.

Xia and Whitesides, "Soft Lithography", *Annu. Rev. Mater. Sci.*, 1998, 28:153-84.

Zelada-Guillen et al. "Label-free detection of *Staphylococcus aureus* in skin using real-time potentiometric biosensors based on carbon nanotubes and aptamers", *Biosensors & Bioelectronics*, 2012, 31:226-32.

Zhu et al. "Graphene and graphene oxide: synthesis, properties, and applications", *Adv. Mater.*, 2010, 22:3906-24.

Zuiderwijk et al., "An amplification-free hybridization-based DNA assay to detect *Streptococcus pneumoniae* utilizing the up-converting phosphor technology", *Clinical biochemistry*, 2003, 36(5):401-3.

* cited by examiner

A

B

SEQUENCE LISTING

```
<160> NUMBER OF SEQ ID NOS: 20

<210> SEQ ID NO 1
<211> LENGTH: 88
<212> TYPE: DNA
<213> ORGANISM: Artificial Sequence
<220> FEATURE:
<223> OTHER INFORMATION: synthetic oligonucleotide

<400> SEQUENCE: 1
gcaatggtac ggtacttcct cggcacgttc tcagtagcgc tcgctggtca tcccacagct      60
acgtcaaaag tgcacgctac tttgctaa                                         88

<210> SEQ ID NO 2
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 2
tatggcggcg tcacccgacg gggacttgac attatgacag                            40

<210> SEQ ID NO 3
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 3
atccgtcaca cctgctctac ggcgctccca acaggcctct ccttacggca tattatggtg      60
ttggctcccg tat                                                         73

<210> SEQ ID NO 4
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 4
```
caaacacacc acgcgcatca gatctgaagc cattggccgt a                41

<210> SEQ ID NO 5
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 5
tgttccgcta tacgccattg gtactgccat aaccttgagc aa               42

<210> SEQ ID NO 6
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 6
agcyagaggc ttatcgctt                                         19

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
ataccgttgg aatctctgcc                                        20

<210> SEQ ID NO 8
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 8
cgatcttgca aaccgccc                                          18

<210> SEQ ID NO 9
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 9
gcagaacgtc aggataaatg ga                                     22

<210> SEQ ID NO 10
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 10
aaccttgagc aatccattta tcctgacgtt ct                          32

<210> SEQ ID NO 11
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 11
ccgccagtga taatccgctt cacactcaac tgggaatccg c          41

<210> SEQ ID NO 12
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 12
tctcgcacat tgttgggaac ggccaggcac cattatcaac agg        43

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
gcgtgcaacc atataggcaa                                  20

<210> SEQ ID NO 14
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 14
agcattccaa ccgcc                                       15

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 15
tgcatcatgc aggtagga                                    18

<210> SEQ ID NO 16
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 16
gcggattccc agttgagtgt gcgtgtac                         28

<210> SEQ ID NO 17
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 17
tgcagtcctc gctcactggg cacg                             24

```
<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 18
cctgctttct ctctcaaga                                                19

<210> SEQ ID NO 19
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 19
ccgcactttc atcttccg                                                 18

<210> SEQ ID NO 20
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 20
gtgatgcaag tgcacctt                                                 18
```

METHODS AND COMPOSITIONS FOR HYBRID MICROFLUIDIC DEVICES INTEGRATED WITH NANO-BIOSENSORS

This application claims priority to U.S. Provisional Patent Application Ser. No. 62/004,260 filed May 29, 2014, which is incorporated herein by reference in its entirety.

STATEMENT REGARDING FEDERALLY FUNDED RESEARCH

This invention as made with government support under Grant No. GM105584 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Infectious pathogens often cause significant economic losses and frequently cause serious public health concerns throughout the world, such as the massive outbreak of a food-borne pathogen *Escherichia coli* O157:H7, which occurred in Japan in 1996 (Michino et al. *Am. J. Epidemiol.* 1999. 150:787-796). Over the past decades, several methods, such as polymerase chain reaction (PCR)-based methods, DNA microarrays, DNA sequencing technology and so on, have been employed for efficient pathogen detection with high specificity. Although these DNA-based approaches have been utilized for pathogen identification, they cannot detect pathogenic microorganisms directly. They either depend on expensive and high-precision instruments (e.g., DNA sequencing), or require cumbersome procedures, such as cell lysis, DNA extraction, amplification and purification.

Immunoassays based on the specific interaction between antibody and antigen can be used for direct pathogen detection. Antibodies, however, are more expensive than oligonucleotides and also can easily become denatured and lose their activities to bind to pathogenic microorganisms.

Pathogen detection technology is vital to the prevention and identification of infectious diseases and biodefense threats. There remains a need for simple, rapid, and sensitive assays for multiplexed detection of pathogens or chemicals.

SUMMARY

Microfluidics is a relatively new technique in the diagnostic research field that offers a unique opportunity for various biomedical applications (Li and Li, 2010, *Expert Review of Clinical Pharmacology*, 3:267-80; Salieb-Beugelaar et al., 2010, *Analytical Chemistry*, 82:4848-64; Kovarik et al., 2011, *Analytical Chemistry*, 84:516-40). Microfluidics provides for minimal reagent consumption, integrated processing, and analysis of complex biological fluids with high efficiency and sensitivity. The devices and methods described herein provide for simple, rapid, and sensitive pathogen detection at low cost. Embodiments include methods and devices for direct pathogen detection.

Certain embodiments are directed to microfluidic biochips that are either a paper-polymer-hybrid system or a fully paper-based system. In certain aspects the biochips are low-cost, sensitive, and fast diagnostic devices for detecting infectious diseases. In certain aspects devices and methods described herein are used for detection of a number of bacterial, fungal, viral, or parasite pathogens. In certain respects the devices and methods can be used to detect bacteria. The devices and methods can be used to detect a number of pathogens simultaneously.

Embodiments of the invention include a polymer/paper hybrid microfluidic system comprising a binding agent, e.g., a probe or aptamer. In certain aspects the polymer is a siloxane polymer such as polydimethylsiloxane (PDMS). The probe or aptamer can be complexed with graphene, graphene oxide (GO), and/or other carbon nanoparticles to form a biosensor. A paper substrate facilitates the integration of biosensors with the device, and avoids complicated surface treatment and aptamer/probe immobilization required for PDMS or glass-only microfluidic systems.

Certain embodiments are directed to devices comprising one or more of (i) a first layer having a microchannel formed in the first layer comprising an inlet reservoir and an outlet connected by a channel, or in certain aspects the first layer has one or multiple wells as reaction (e.g., amplification) wells; (ii) a second layer having at least one detection well that is in or can be brought into fluid communication with a microchannel of the first layer; in certain aspects, structures on the first and second layer can be integrated into a single layer; (iii) a third layer can form a floor of the microwell of the second layer; in certain aspects this layer can be eliminated by configuring the second layer microwells with a bottom; and (iv) a paper insert positioned in the detection microwell. In certain aspects the device comprises a plurality of detection microwells with an associated paper insert. In a further aspect the paper insert is configured to have the edges of the paper insert positioned along the walls of the microwell and the bottom of the insert in contact with the floor of the microwell.

In certain aspects the microfluidic biochip can comprise 1, 2, 3, 4, 5, 6, 7 8, 9, 10, 15, 20 or more microwells or chambers. A microwell can be 0.5, 1, 2, or 3 mm in diameter, including all values there between and 1, 2, 3, or 4 mm in depth, including all values there between. In certain aspects the device can be loaded without using complicated surface modification procedures for aptamer/probe immobilization. An aptamer/probe mixture can be preloaded into detection microwells. In certain aspects an aptamer/probe is coupled to a detectable label, e.g., a fluorescent label. In a further aspect an aptamer/probe can be reversibly complexed or absorbed in a quenching moiety that dissociates from the aptamer/probe forming, activating, or permit generation of a detectable signal, e.g., fluorescence of a fluorescent moiety). In certain aspects a quenching moiety is manganese or, graphene, graphene oxide and carbon nanoparticles.

In a further aspect, the microwells can be arranged in an array. In certain aspects the array is, but need not be, a regular array such as a linear or radial array. In certain aspects the microwell array can be arranged in a 1, 2, 4, 6, 8, 10, 12 or more rows by 1, 2, 4, 6, 8, 10, 12 or more columns. In a further aspect the array can be arranged in 2, 4, 5, 8, 10, 12 or more radii. A horizontal cross section of the microwell can form any geometric shape, such as a circular, square, rectangle, triangle, etc. In certain aspects the microwell has a circular horizontal cross section. In a further aspect the microwell is 0.5, 1, 2, 3 mm in diameter, including all values there between and 1, 2, 3, 4 mm in depth, including all values there between. In certain aspects the microwell can have a flat or rounded floor.

In certain aspects a device can be loaded without using complicated surface modification procedures for aptamer/ probe immobilization. The paper insert integrates the aptamer/probe-functionalized GO biosensor into the microfluidic chip. A GO-aptamer/probe mixture can be introduced into microwells through microchannels in an additional reagent-introduction layer before the top layer is bonded with the middle layer (pre-loaded). The GO-aptamer/probe will be adsorbed and stored on the paper insert. The high surface-to-volume property of the porous paper improves reaction kinetics for rapid assays. In certain aspects the reagent-introduction layer will be replaced with a polymer layer comprising one or more channels for sample loading after the GO-aptamer introduction. Once the paper is dry, the device is ready to use. A test sample can then be loaded into the microwells by using microchannels in the device. In certain aspects the microwell is configured as a biosensor that directly binds a pathogen target or an analyte produced using another reaction, such as nucleic acid amplification or other enzymatic modification. In certain embodiments pathogens are directly detected without any complicated DNA treatment such as DNA extraction, amplification, and/or purification. In other embodiments a sample is introduced into a reaction well that transforms the sample. The product of the reaction well can then be transferred to a detection well for detection of one or more targets in the sample. Therefore, embodiments of the device provide a one-step or multi-step mechanism with high sensitivity for pathogen detection.

Certain embodiments are configured to amplify and detect nucleic acids of one or more pathogens as an indicator of the presence of one or more pathogens. In one aspect at least one microwell is configured as an amplification well. In certain aspects the amplification well will comprise one or more primer pairs, with each primer pair being specific for a pathogen or a family or genus of microbes. A test sample can be loaded into the amplification well. In certain embodiment pathogens are or are not exposed to DNA treatment such as DNA extraction and/or purification. The amplification well can also include enzymes, substrates, and other components for amplification. Therefore, embodiments of the device provide a high-sensitivity detection mechanism for pathogen detection.

Other embodiments are directed to an amplification microfluidic device with, optionally, at least a second chamber for detection. In certain aspects a microfluidic system has an amplification chamber configured to amplify nucleic acids and detect amplified nucleic acids in the detection chamber. The amplification chamber can be configured so that after the amplification process the amplified sample is transferred to one or more detection zones. In certain aspects the amplification reaction is delivered to detection wells by rotating the reaction well to sequentially fill a plurality of detection wells. In certain aspects, nucleic acid amplification methods can be loop-mediated isothermal amplification (LAMP) or other isothermal gene amplification methods. The detection moiety in detection wells can be a probe that binds an amplification product or other chemical that reacts or is transformed after amplification occurs in the amplification well. In certain aspects one amplification wells can be used for multiplexed DNA amplification. This embodiment can be referred to as a dual-purpose chamber microdevice. In other aspects one or more specific hybridization probes can be included in a detection well that binds to a specific amplified nucleic acids.

Another embodiment is directed to a microdevice that has one chamber for sample manipulation (reaction chamber or well) and at least a second chamber for detection (detection chamber or well). The reaction chamber or well can be configured so that after the reaction process the reaction product is transferred to one or more detection zones, chambers, or wells. The detection well will have one or more specific probes that will specifically bind a target analyte derived from a pathogen or class of pathogen. Certain embodiments are directed to a detector configured to detect the presence of a target by detecting the interaction between a probe and the target using a biosensor described herein.

Certain embodiments are directed to methods of detecting a pathogen(s) comprising introducing a sample suspected of having or comprising a target pathogen(s) into a device described herein. Subjecting the sample to detection or manipulation and detection, wherein if a target is present in the sample an analyte binds to a probe and produces a detectable signal.

In certain aspects the device is configured to detect a plurality of targets at once (multiplexed assay) with a separate and distinct probe in an individual detection microwell, or separate and distinguishable probes in the same microwell. In certain aspects a single detection microwell can have two or more probes that can be distinguish from each other. In certain aspects the target is a pathogen, such as a food borne pathogen or other etiologic agent. The pathogen can be a bacteria, a fungus, a parasite, a virus, or combinations thereof.

A microfluidic device or components thereof (e.g., top, middle, and/or bottom layer) can be made from any suitable material or materials. For example, the device or components thereof may be fabricated from inorganic materials including paper, glass, silica, silicon, metal, or the like, or plastics or polymers, including dendritic polymers, such as poly(vinyl chloride), poly(vinyl alcohol), poly(methyl methacrylate), poly(vinyl acetate-maleic anhydride), poly(dimethylsiloxane)monomethacrylate, cyclic olefin polymers and copolymers including copolymers of norbornene and ethylene, fluorocarbon polymers, polystyrenes, polypropylene, polyethyleneimine; copolymers such as poly(vinyl acetate-co-maleic anhydride), poly(styrene-co-maleic anhydride), polysaccharide, polysaccharide peptide, poly(ethylene-co-acrylic acid) or derivatives of these or the like. The materials for forming the devices or components or parts thereof may be selected based on desired mechanical or other properties for optimizing target detection. In certain aspects the device is made of a polymer, such as, but not limited to polysiloxane (e.g., polydimethysiloxane (PDMS)); polymethyl-methacrylate (PMMA), polycarbonate (PC), or cyclic olefin copolymer (COC). In further aspects the middle layer (if present) is a siloxane polymer, such as, but not limited to polydimethysiloxane (PDMS). In certain aspects the bottom layer is glass, PMMA, PDMS, PC, or COC. In certain embodiments all layers are paper.

In certain aspect components of the device can be made or paper. In certain aspects a device can comprise a paper insert or floor. The particular characteristics of the paper insert can vary as long as the paper insert adsorbs the aptamer/probe and/or the aptamer/probe-graphene oxide/graphene/carbon nanoparticle composition. As used herein adsorption is the adhesion of molecules to a surface. This process creates a film of the adsorbate (e.g., aptamer/aptamer+graphene oxide) on the surface of the adsorbent (paper insert). This process differs from absorption, in which a fluid (the absorbate) permeates or is dissolved by a liquid or solid (the absorbent). Adsorption is a surface-based process while absorption involves the whole volume of the material.

Paper is a thin material produced by pressing together moist fibers, typically cellulose pulp derived from wood or grasses and drying them into flexible sheets. The thickness of paper is often measured by caliper, which is typically given in thousandths of an inch. Paper is often characterized by weight. In the United States, the weight assigned to a paper is the weight of a ream (500 sheets) before the paper is cut to size. For example, a ream of 20 lb, 8.5 in ×11 in (216 mm×279 mm) paper weighs 5 pounds, because it has been cut from a larger sheet into four pieces. The density of paper ranges from 250 kg/m$^3$ (16 lb/cu ft) for tissue paper to 1,500 kg/m$^3$ (94 lb/cu ft) for some specialty paper. In certain aspect the paper insert is a porous blotting paper having a thickness of 0.5 to 2 mm, including all values there between. In a further aspect the paper insert is chromatography paper having a thickness 0.05 to 0.25 mm and pores having a diameter of 5 to 15 µm. In certain embodiments an aptamer is absorbed onto and/or into the paper insert. In certain aspect an aptamer or probe is coupled to a fluorescent label. In a further aspect the aptamer or probe is reversibly complexed or adsorbed in a quenching moiety that dissociates from the aptamer or probe when the aptamer or probe binds its target. In certain aspects the quenching moiety is graphene oxide, graphene, or carbon nanoparticle.

Certain embodiments are directed to a detector configured to detect the presence of a target by detecting the interaction between an aptamer or probe, and the target using a device and/or biosensor described herein.

The term "probe" refers to a molecule that can detectably distinguish between target molecules differing in structure/ nucleic acid sequence. Detection can be accomplished based on identification of specific binding with a target. Examples of such specific binding include nucleic acid probe hybridization. Thus, for example, probes can include nucleic acid hybridization probes, for example DNA, RNA, PNA, pseudo-complementary PNA (pcPNA), locked nucleic acid (LNA) and nucleic acid analogs thereof.

Oligonucleotides can be used as "probes", and refer to e.g., genomic DNA, mRNA, or other suitable sources of nucleic acid oligonucleotides. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions. In certain aspects a nucleic acid probe is 10, 20, 30, 40, 50, 60 nucleotides in length, including all values and ranges there between.

As used herein, the term "aptamer" refers to a biopolymer material that binds in three-dimensions to a specific target molecule, protein, or other target in the form of single-stranded or double-stranded DNA or RNA. Typically, aptamers are small nucleic acids ranging from 15-50 bases in length that fold into defined secondary and tertiary structures, such as stem-loops. It is preferred that the aptamers bind the target high-expression or low-expression protein with a $k_d$ less than $10^{-6}$, $10^{-8}$, $10^{-10}$, or $10^{-12}$ M. Aptamers can bind the target with a very high degree of specificity. Aptamers may be comprised of multiple ribonucleotide units, deoxyribonucleotide units, or a mixture of both types of nucleotide residues. In addition, aptamers may further comprise one or more modified bases, sugars or phosphate backbone units.

The phrase "specifically binds" to a target refers to a binding reaction that is determinative of the presence of the molecule, microbe, or other targets in the presence of a heterogeneous population of other biologics. Thus, under designated assay conditions, a specified molecule binds preferentially to a particular target and does not bind in a significant amount to other biologics present in the sample. Specific binding of an aptamer or probe to a target under such conditions requires the aptamer or probe be selected for its specificity to the target. A variety of assay formats may be used to select aptamers or probes specifically reactive with a particular target.

As used herein, the term "sample" or "test sample" generally refers to a material suspected of containing one or more targets, e.g., pathogens. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, lysing microbes in the sample, and the like. Methods of treatment may involve filtration, precipitation, dilution, distillation, mixing, concentration, inactivation of interfering components, lysing organisms and/or cells, and the addition of reagents. Besides physiological fluids, other liquid samples may be used such as water, food products, and the like for the performance of environmental or food production assays. In addition, a solid material suspected of containing the target may be used as the test sample. In some instances it may be beneficial to modify a solid test sample to form a liquid medium or to release a target (e.g., a nucleic acid).

The term "analyte" or "target analyte" refers to a compound or composition to be detected or measured in the test sample. The analyte will bind a probe, aptamer, or other detection reagents. An analyte can be an antigenic substance, hapten, antibody and combination thereof. The analyte of interest in an assay can be, for example, a protein, a peptide, an amino acid, a nucleic acid, a hormone, a steroid, a vitamin, a pathogenic microorganism, a natural or synthetic chemical substance, a contaminant, a drug, or metabolite.

Other embodiments are discussed throughout this application. Any embodiment discussed with respect to one aspect applies to other aspects as well and vice versa. Each embodiment described herein is understood to be embodiments that are applicable to all aspects. It is contemplated that any embodiment discussed herein can be implemented with respect to any method or composition of the invention, and vice versa. Furthermore, compositions and kits of the invention can be used to detect pathogens and other targets.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Microfluidic lab-on-a-chip techniques have attracted significant attention in the past two decades because of the variety of advantages associated with miniaturization, integration, and automation. The ease and low-cost of soft lithography have made polydimethylsiloxane (PDMS)-based microfluidic devices the dominant platform in microfluidic bioapplications. However, PDMS and glass microdevices are often associated with additional complicated chemical surface modifications for probe immobilization. Recently, paper-based microfluidic devices have been described that provide a new low-cost platform for different applications in low-resource settings. Paper-based microfluidic devices, however, typically do not offer the high level of performance and functionality that PDMS affords in liquid flow control and delivery. Therefore, taking the advantages from both paper and PDMS substrates, herein, a simple polymer/paper hybrid microfluidic system for fast multiplexed pathogen detection is described. The introduction of porous paper materials inside, for example, PDMS-fabricated microwells provides a simple and efficient strategy for immobilization of various molecules without the need for chemical surface modifications. Also described is an integrated one-step aptamer/probe-functionalized graphene oxide (GO) biosensors on the chip, using a sensitive "turn on" strategy based on the fluorescence quenching and recovering propriety of GO when adsorbing and desorbing fluorescent labeled aptamers or probes.

I. MICROFLUDIC DEVICES

Microdevices described herein can comprise one or more microwells configured for pathogen detection. In certain aspects one or more microwells are in fluid communication with one or more microchannels and/or reservoirs. In certain aspects a microwell can comprise a paper based biosensor for the direct or indirect detection of one or more pathogen. In certain aspect one well can be a reaction well and a second well a detection well. Each of the wells can be reversibly sealed to form a chamber. In another aspect the a microchannel can be modified to form a reaction or detection zone that acts on a sample as it flows through the zone.

Figures 1A, 1B, 1C:
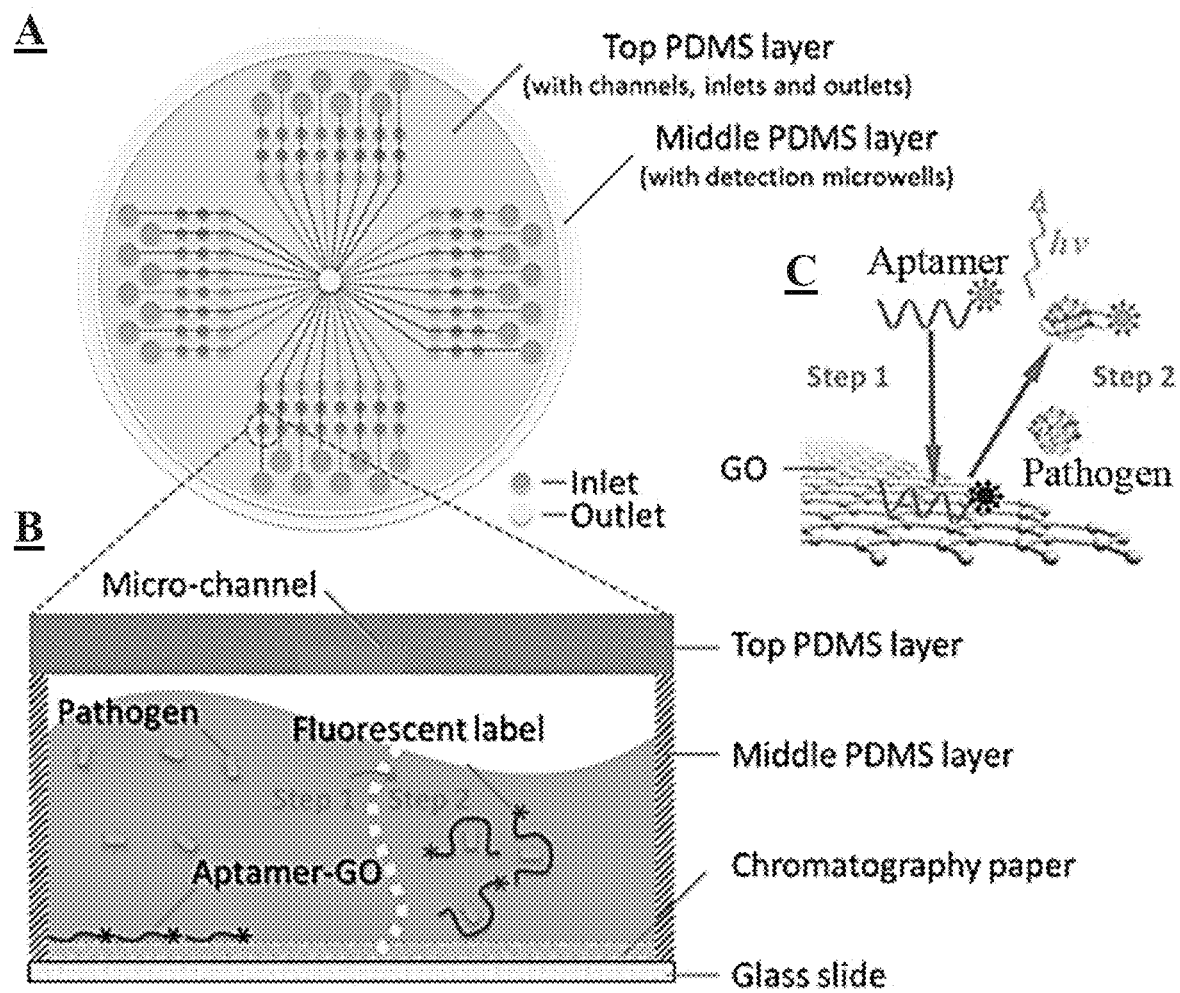
FIG. 1A-1C. Illustration of the PDMS/paper hybrid microfluidic system for one-step multiplexed pathogen detection using aptamer functionalized GO biosensors. (A) Microfluidic device layout. (B) and (C) illustrate the principle of the one-step 'turn-on' detection based on the interaction among GO, aptamers and pathogens. Step 1: when an aptamer is adsorbed on the GO surface, its fluorescence is quenched. Step 2: when the target pathogen is present, the target pathogen induces the aptamer to be liberated from GO and thereby restores its fluorescence for detection.

One embodiment of a microfluidic device is illustrated in FIG. 1 and FIG. 2. The described microfluidic system can multiple features, including: (1) Simplicity. The detection of pathogenic microorganisms may require only a one step detection procedure based on integrated aptamer functionalized GO biosensors. In addition, this approach detects pathogen microorganisms directly, without cumbersome sample preparation procedures, making it feasible for field detection. (2) The polymer/paper hybrid microfluidic system can combine advantages from both substrates. For instance, the paper substrate facilitated biosensor immobilization, and avoids complicated surface treatment and aptamer/probe immobilization. (3) The approach is fast. The assay takes only ~10 min once a ready-to-use microfluidic device is prepared. A 96-well array configuration in a microfluidic system also aims at high throughput. Detection can be accomplished using a cellular phone camera and colorimetric detection can provide an option for resource-limited settings. (4) Such a system has potential in the rapid detection of a wide variety of pathogens, including plant, animal, food-borne, biodefense, and other infectious diseases.

Other embodiments include a microfluidic device for pathogen detection comprising at least two layers. The first layer can be a polymer layer used for reagent delivery, for example, one or more micro-channels (e.g., length 10 mm, width 100 µm, depth 100 µm) can be formed in the first layer. The first layer can also have an inlet/reservoir (e.g., diameter 1.0 mm, depth 1.5 mm). The second layer can be a detection layer having two or more detection wells, outlet reservoirs (e.g., diameter 1.0 mm, depth 1.5 mm), and micro-channels (e.g., length 9.5 mm, width 100 µm, depth 100 µm). In certain aspect a device can include a support layer (e.g., a glass slide (length 75 mm, width 25 µm, depth 1.0 µm). Different detection wells can be used for negative control (NC), positive control (PC), and pathogen detection. The device can be configured in any number of geometries include rectangular, square, triangular, or circular.

The detection portion of the device comprises probes for target pathogens/analytes or controls that can be pre-loaded in a detection well. In a further aspect, a reaction product is transferred to a separate detection zone, e.g., by puncturing a wall or floor of a reaction chamber and allowing the flow of reaction product to a detection region of the device, or by movement of two or more layers to establish fluid communication between reaction wells and detection wells. A device can be configured to transport a reaction mixture and/or sample from an inlet to fill the reaction well(s)/chamber(s)/zone(s). In certain aspect a filter is included in the device and positioned such that a sample being applied to the device is filtered prior to being transported to a reaction well/chamber/zone. After filling, the inlet and outlets can be sealed or closed, e.g., with epoxy or movement of the layers. A reaction is then performed for an appropriate amount of time.

Microfluidic devices and systems, because of their extremely small space requirements are particularly well suited for parallelization or multiplexing because large numbers of parallel analytical fluidic elements can be combined within a single integrated device that occupies a relatively small area. A parallelized or multiplexed device can be configured for high throughput screening assays. A multiplexing system will comprise a plurality of channels and microwells that are configured to analyze a number of different pathogens.

Figures 8A, 8B, 8C:
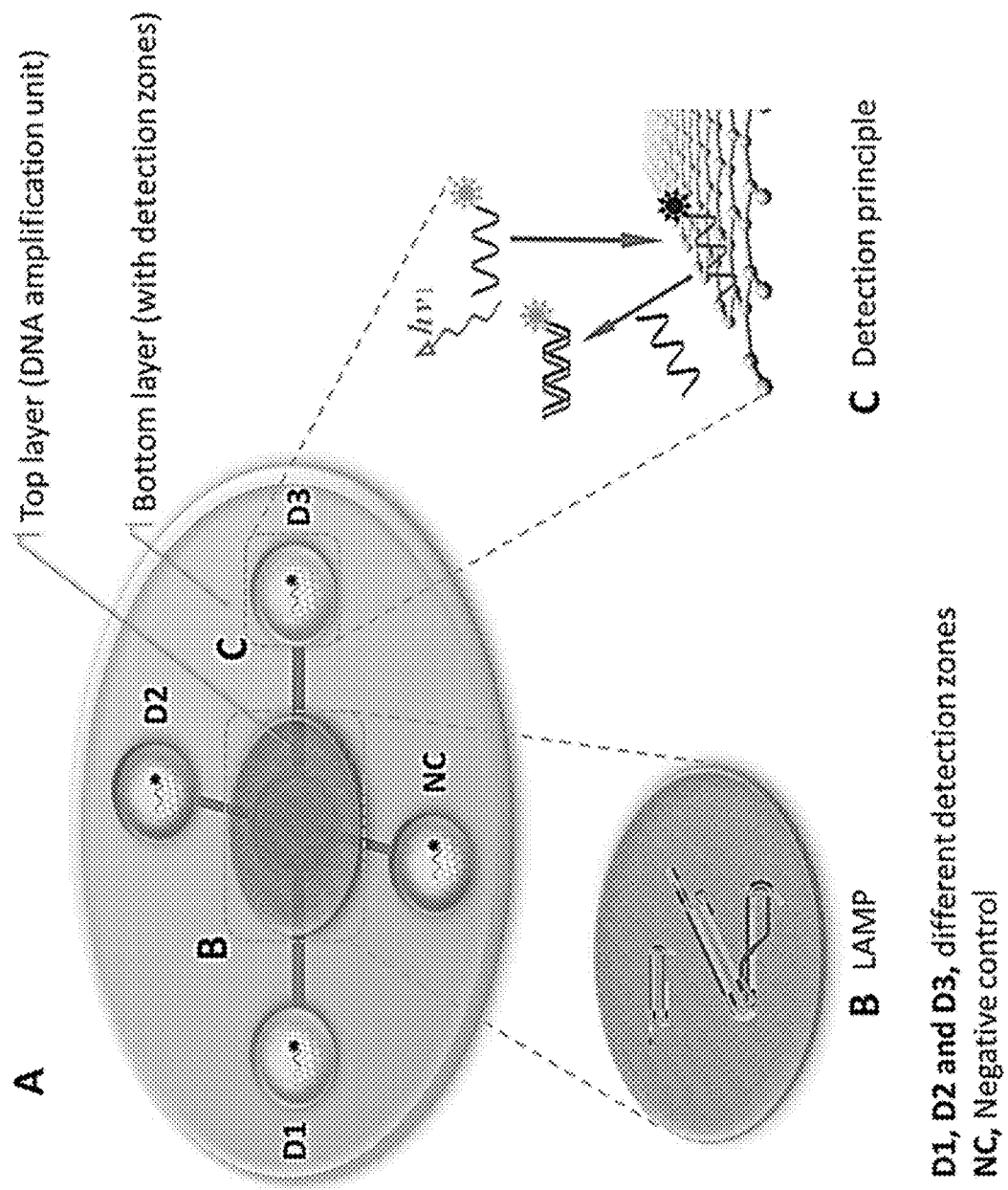
FIG. 8A-8C (A-C) Schematic of low-cost and multiplex detection of meningitis causing pathogens on paper-based 3D microfluidic devices. There are two layers in the microfluidic system. DNA amplification unit—LAMP is carried out in the top layer. (C) Illustration of detection principle using graphene-oxide nano-material. Fluorescence of fluorophore-labeled probes is quenched when probes are adsorbed on the surface of grapheme oxide (GO). In contrast, when the target DNA is present, the quenched fluorescence is restored.

In certain embodiments a paper-based microfluidic device may comprise at least two layers (FIG. 8), one layer having an amplification chamber and a second layer having a detection zone. The first layer can be nucleic acid amplification unit. The second layer including microchannels and detection zones. In certain aspects the second layer comprises 2, 3, 4, 5, 6, or more microchannels. The microchannels can be in fluid communication with 2, 3, 4, 5, 6 or more detection zones. Each detection zone can have one or more detectable probes. In certain aspects the detectable moiety of the detectable probe is quenched. In certain aspects the detectable moiety is quenched by graphene oxide (GO), graphene or carbon nanoparticles. In certain aspects these nanomaterials can be physically adsorbed on the paper surface.

To increase the detection sensitivity and avoid contamination during sample transfer, certain embodiments have a nucleic acid amplification unit or amplification chamber/zone integrated on the device. This well, chamber, unit, or zone can be provided on a separate layer providing flexibility in sample handling. In certain aspects the bottom of the DNA amplification zone is sealed, for example with a thin layer of adhesive tape or positioned over a moveable capping portion of another layer, and the top is covered with a tape layer, a cap, or mineral oil to prevent liquid evaporation. Samples can be isothermally amplified on a thin film heater by LAMP (Ahmad et al. (2011) *Biomed Microdevices*, 13(5): 929-37). In certain aspects, a portable heating system based on a proportional-integral-derivative (PID) temperature controller, a thermocouple and a heating film can be used. A battery-powered portable heating system has been developed for field detection. During the DNA amplification process, the pathogen DNA can be labeled with fluorophores for DNA fluorescence detection in a later step.

Figure 9:
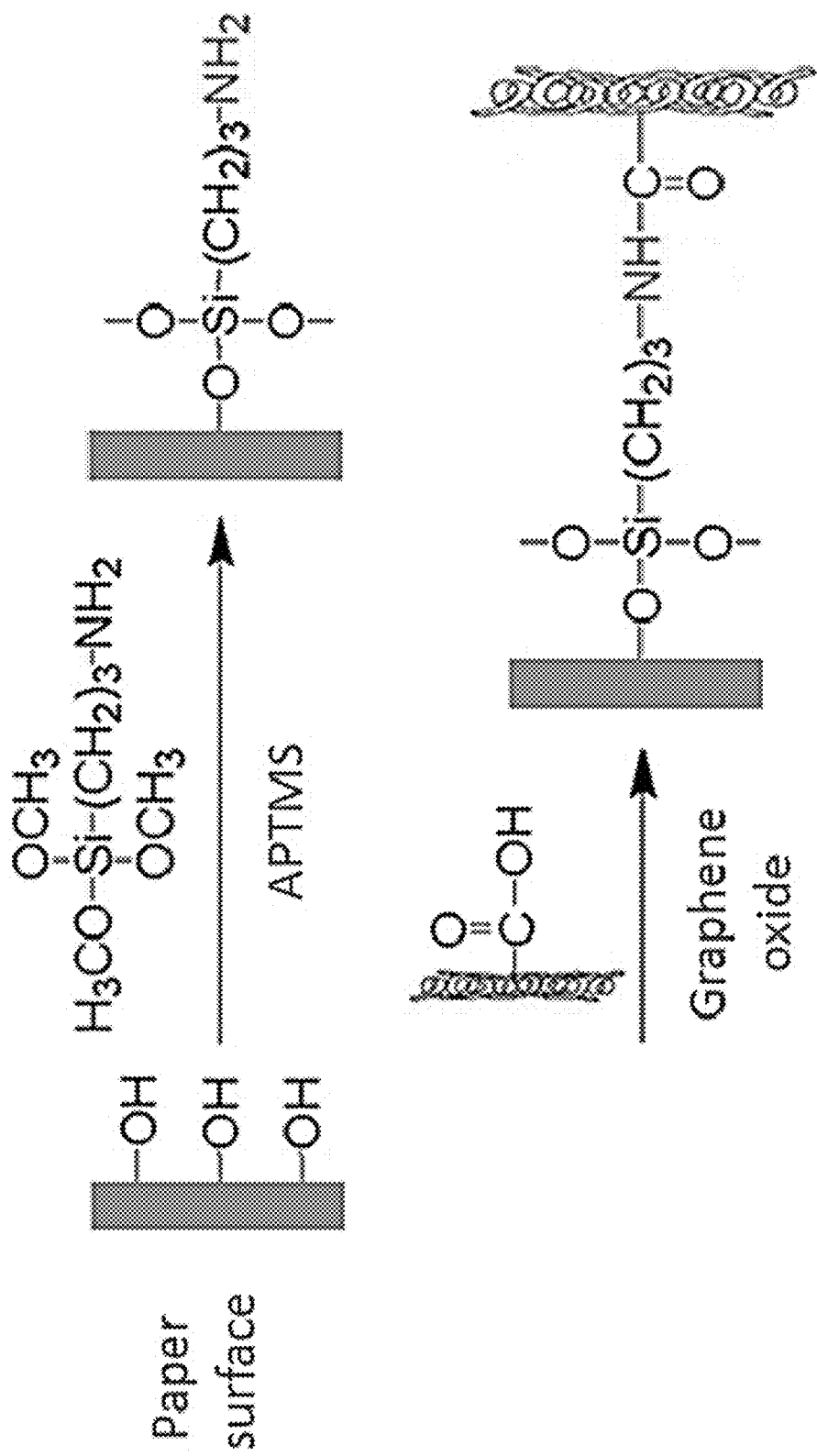
FIG. 9. Surface modification of cellulose paper to link GO to paper. 3-aminopropyl-trimethoxysilane (APTMS) is immobilized on the paper surface via the linkage with hydroxyl groups on paper. The reaction of carboxyl groups from GO with amine groups from APTMS leads to the covalent attachment of GO on the paper surface.

Certain aspects described herein link graphene oxide (GO) covalently to the paper substrate by surface modification of paper, as shown in FIG. 9. 3-aminopropyl-trimethoxysilane (APTMS) is immobilized on the paper surface by linkage with hydroxyl groups. The reaction of carboxyl groups from GO with amine groups from APTMS leads to the covalent attachment of GO on the paper surface. Once GO is linked to the paper in the detection zones, it will provide a platform on which to immobilize various probe oligonucleotides (e.g., 5'-CCTGCTTTCTCTCTCAAGA-3' (SEQ ID NO:18), 5'-CCGCACTTTCATCTTCCG-3'(SEQ ID NO:19), 5'-GTGATGCAAGTGCACCTT-3'(SEQ ID NO:20), for *N. meningitidis, H. influenzae* and *S. pneumonia*, respectively, for multiplex DNA sensing. ssDNA labeled with fluorophores can self-assemble onto the surface of GO to form a stable ssDNA-GO architecture, and its fluorescence will be quenched (Loh et al., 2010, *Nat Chem*, 2(12):1015-24).

After incubation in a reaction chamber, a seal can be penetrated or opened, and fluid communication with a channel on the bottom layer established. In certain aspects analyte or reaction product flow to different detection zones via the wicking effect of paper, position of the wells with respect to each other, or microchannel flow. Paper can provide a simple strategy to actuate liquid flows in paper, without off-chip controllers and power. This feature can be useful for detection in the field and other resource-limited settings. Specific probes targeted to different pathogens or analytes can be pre-adsorbed in the detection zones (e.g., via GO), allowing the detection of pathogens or analytes simultaneously and selectively.

Certain embodiments incorporate a miniaturized portable fluorescence detection system using a light emitting diode (LED), such as violet LED (Tsai et al., 2003, *Electrophoresis*, 24(17):3083-88), a UV LED, or a green laser pointer. The wavelength of 532 nm from a green laser pointer is a good fit with the excitation wavelength of one of the common probes—Cy3, but other combinations of light source and fluorophore can be used. A brief comparison among different diagnostic approaches is listed in Table 1.

TABLE 1

Comparisons among different diagnostic approaches

| | Chip material cost | Heating system | Detection | For resource-poor settings | Time needed |
|---|---|---|---|---|---|
| Ours | ~5 cents | ~$100 | ~$200 | Yes | <60 min |
| RT-PCR | N/A | ~$65,000 | | No | 2-30 hours |
| Cell culture | N/A | ~$7,000, incubators | ~$6,000 | No | >48 hours |

In certain embodiments a filtration layer can be included to remove red blood cells in order to avoid detection inference in subsequent steps.

In certain embodiments a microfluidic device is configured for meningitis diagnosis in a laboratory or home setting. In other embodiments a microfluidic device is configured to provide a POC device for field diagnosis. Furthermore, the microfluidic devices and methods can be used to detect various plant, animal, food-borne, and other infectious diseases (e.g., *B. pertussis*, HIV) in resource-limited settings.

Colorimetric detection can be enhanced by UV light from UV LED, gold nanoparticles, quantum dots (QDs) (Edgar et al., 2006, *Proc Natl Acad Sci USA*, 103(13):4841-45; Smith et al., 2006, *Expert Rev Mol Diagn*, 6(2):231-44), and silver enhancement (Taton et al., 2000, *Science*, 289(5485):1757-60) can be used as detectable moieties. Gold nanoparticles promote the reduction of $Ag^+$, resulting in the color change from white to black on paper.

In certain aspects GO is immobilized on the paper surface to adsorb DNA capture probes. If the efficiency of GO immobilization on paper is sufficient, a covalent immobilization of DNA capture probes can be used to graft DNA codes on paper.

Certain embodiments of the device are in the form of a microfluidic rotary chip (termed as SpinChip herein), (FIG. 10), the microfluidic SpinChip has at least two plates attached to each other (e.g., by an adjustable attachment), in certain aspects the plates can be attached at the center. The bottom plate (FIG. 10a-2) can be configured to contain a reaction or LAMP zone. The top plate (FIG. 10a-1) can be configured to contain a plurality of detection zones with a paper disk placed inside, in which GO nanosensors (or graphene, carbon nanoparticles) functionalized with labeled probes are preloaded. The detection zones can, for example, be divided into areas used for *N. meningitidis* and *S. pneumoniae* detection (N.M. and S.P.) with their corresponding probes, as well as negative controls (NC1 and NC2). NC1 can be preloaded with a non-target probe, Influenza A probe, as a negative control; No probe can be preloaded for NC2. In addition, there an inlet can be provided in the top plate, where samples can be introduced into the LAMP zone on the bottom plate.

The fabrication of hybrid microfluidic SpinChips is fast, simple and it is easy to operate. All LAMP zone, detection zones and chromatography paper disks can be directly cut by a laser cutter (Epilog Zing 16, Golden, Colo.) in a matter of minutes. The bottom plate with LAMP zone can be exposed in an oxidizing air Plasma cleaner for 30 seconds, making the LAMP zone hydrophilic. A chromatography paper was tightly placed inside each detection zone as a 3D storage substrate for the GO nano-biosensors. The chromatography paper inside the detection zones absorbed GO and probe solutions by capillary effect. First, 0.8 µL 0.04 mg/mL GO was added into each detection zone. After it became dry in 5 minutes at room temperature, 0.8 µL probe solution was then added into each detection zone and was left to dry at room temperature in another 5 minutes. The two plates were then tightened together with a screw in the center of both plates. Then, the hybrid microfluidic SpinChip becomes ready to use.

II. TARGET DETECTION

Certain embodiments include devices and compositions comprising one or more biosensors. A biosensor as used herein comprises an aptamer that specifically binds a target that is coupled to a reporter moiety and a quenching moiety, wherein the fluorescent moiety is quenched in the absence of a target molecule and when bound to a target molecule that quenching is suppressed or release. The biosensors of the composition may be specific for different target molecules, and may be associated with the same or different reporter molecules.

In another embodiment, two or more biosensors may be immobilized onto a substrate at spatially addressable locations. The biosensors may be specific for different target molecules and may be associated with the same or different reporter molecules.

In another aspect, the application provides a method for detecting at least one target molecule comprising providing at least one biosensor comprising a selectivity component and a reporter molecule and detecting the signal of the reporter molecule, wherein interaction of the biosensor with the target molecule produces a detectable change in the signal of the reporter molecule. In various other aspects, the biosensors of the invention may be used for the detection of environmental pollutants, hazardous substances, food contaminants, and biological and/or chemical warfare agents.

In various embodiments, the biosensors of the invention may be used to detect target molecules, including, for example, cells, microorganisms (bacteria, fungi and viruses), polypeptides, nucleic acids, hormones, cytokines, drug molecules, carbohydrates, pesticides, dyes, amino acids, small organic molecules and small inorganic molecules.

Biosensors may be used for the detection of target molecules both in vivo and in vitro. In certain embodiments, the biosensor may be injected or implanted into a patient and the signal of the reporter molecule is detected externally. In one exemplary embodiment, the biosensors of the application may be used for the detection of intracellular targets. In another exemplary embodiment, the biosensors of the application may be attached to a fiber optic probe to facilitate position of the biosensor within a sample and readout from the biosensor through the optical fiber.

In still other embodiments, the biosensor may be expressed directly into the cell, tissue or subject to be analyzed. Using molecular biology methods, a vector comprising at least a gene encoding a selectivity component is constructed and inserted into the host, resulting in expression of the selectivity component, as described in more detail below.

Various, more detailed embodiments of and methods for producing the selectivity component and reporter molecule components are also further described below.

A. Aptamers

Aptamers, oligonucleotides or peptide molecules that bind to a specific target molecule, have shown promising applications in diagnostics and therapeutics. Unlike antibodies, aptamers are stable, and the chemical nature of nucleic acids allows easy synthesis and modification of aptamers. Aptamers can bind directly to pathogens similar to antibodies. Various aptamer-based biosensors have been developed for pathogen detection, commonly using fluorescent or electrochemical detection. However, they either need complicated procedures for surface treatment, probe immobilization, and/or sample loading and cannot provide multiplexed detection.

Traditionally, techniques for detecting and purifying target molecules have used polypeptides, such as antibodies, that specifically bind such targets. Nucleic acids have long been known to specifically bind other nucleic acids (e.g., nucleic acids having complementary sequences). However, nucleic acids that bind non-nucleic target molecules have been described and are generally referred to as aptamers. See, e.g., Blackwell et al. *Science* (1990) 250:1104-1110; Blackwell et al. *Science* (1990) 250:1149-1152; Tuerk and Gold *Science* (1990) 249:505-510; Joyce *Gene* (1989) 82:83-87. As applied to aptamers, the term "binding" specifically excludes the "Watson-Crick"-type binding interactions (i.e., A:T and G:C base-pairing) traditionally associated with the DNA double helix. The term "aptamer" thus refers to a nucleic acid or a nucleic acid derivative that specifically binds to a target molecule, wherein the target molecule is either (i) not a nucleic acid, or (ii) a nucleic acid or structural element thereof that is bound by the aptamer through mechanisms other than duplex- or triplex-type base pairing.

In general, techniques for identifying aptamers involve incubating a preselected non-nucleic acid target with mixtures (2 to 50 members), pools (50 to 5,000 members) or libraries (50 or more members) of different nucleic acids that are potential aptamers under conditions that allow complexes of target molecules and aptamers to form. By "different nucleic acids" it is meant that the nucleotide sequence of each potential aptamer may be different from that of any other member. The sequences are selected and become increasingly less randomized and consensus sequences may appear; in any event, it is preferred to ultimately obtain an aptamer having a unique nucleotide sequence that displays an appropriate binding affinity and/or specificity.

Aptamers and pools of aptamers are prepared, identified, characterized and/or purified by any appropriate technique, including those utilizing in vitro synthesis, recombinant DNA techniques, PCR amplification, and the like. After their formation, target:aptamer complexes are then separated from uncomplexed members of the nucleic acid mixture, and the nucleic acids that can be prepared from the complexes are candidate aptamers (at early stages of the technique, the aptamers generally being a population of a multiplicity of nucleotide sequences having varying degrees of specificity for the target). The resulting aptamer (mixture or pool) can then substituted for the starting aptamer (library or pool) and the steps repeated any number so times. When a limited number (e.g., a pool or mixture, preferably a mixture with less than 10 members, most preferably (1) of nucleic acids having satisfactory specificity is obtained, the aptamer is sequenced and characterized. Pure preparations of a given aptamer are generated by any appropriate technique (e.g., PCR amplification, in vitro chemical synthesis, and the like).

For example, Tuerk and Gold (*Science* (1990) 249: 505-510) describe the use of a procedure termed "systematic evolution of ligands by exponential enrichment" (SELEX). In this method, pools of nucleic acid molecules that are randomized at specific positions are subjected to selection for binding to a nucleic acid-binding protein (see, e.g., PCT Publication WO 91/19813 and U.S. Pat. No. 5,270,163, each of which is incorporated herein by reference). The oligonucleotides so obtained are sequenced and otherwise characterization. Kinzler et al. (*Nucleic Acids Res.* (1989) 17:3645-3653) used a similar technique to identify synthetic double-stranded DNA molecules that are specifically bound by DNA-binding polypeptides. Ellington et al. (*Nature* (1990) 346: 818-822) describe the production of a large number of random sequence RNA molecules and the selection and identification of those having a particular binding specificity.

Another technique for identifying nucleic acids that bind non-nucleic target molecules is the oligonucleotide combinatorial technique described by Ecker et al. (*Nucleic Acids Res.* 21, 1853 (1993)) known as "synthetic unrandomization of randomized fragments" (SURF), which is based on repetitive synthesis and screening of increasingly simplified sets of oligonucleotide analogue libraries, pools and mixtures. The starting library consists of oligonucleotide analogues of defined length with one position in each pool containing a known analogue and the remaining positions containing equimolar mixtures of all other analogues. With each round of synthesis and selection, the identity of at least one position of the oligomer is determined until the sequences of optimized nucleic acid ligand aptamers are discovered.

Once a particular aptamer has been identified through a SURF, SELEX or any other technique, its nucleotide sequence can be determined (as is known in the art), and its three-dimensional molecular structure can be examined by nuclear magnetic resonance (NMR). Selected aptamers may be resynthesized using one or more modified bases, sugars or backbone linkages. Aptamers consist essentially of the minimum sequence of nucleic acid needed to confer binding specificity, but may be extended 5', 3', or from both ends, or may be otherwise derivatized or conjugated.

B. Reporter Moiety

Aptamers can be coupled to a variety of reporter moieties. Reporter moieties include fluorescent reporter moieties that can used to detect aptamer binding to a target. Fluorophores can be fluorescein isothiocyanate (FITC), allophycocyanin (APC), R-phycoerythrin (PE), peridinin chlorophyll protein (PerCP), Texas Red, Cy2, Cy3, Cy3.5, Cy5, Cy5.5, Cy7; or fluorescence resonance energy tandem fluorophores such as PerCPCy5.5, PE-Cy5, PE-Cy5.5, PE-Cy7, PE-Texas Red, and APC-Cy7. Other fluorophores include, Alexa Fluor® 350, Alexa Fluor® 488, Alexa 25 Fluor® 532, Alexa Fluor® 546, Alexa Fluor® 568, Alexa Fluor® 594, Alexa Fluor® 647; BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665; Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, and tetramethylrhodamine, all of which are also useful for fluorescently labeling aptamers.

C. Quenching Moiety

Quenching refers to any process that decreases the fluorescence intensity of a given substance. A variety of processes can result in quenching, such as excited state reactions, energy transfer, complex-formation, and collisional quenching. Molecular oxygen, iodide ions, and acrylamide are common chemical quenchers. The chloride ion is a well-known quencher for quinine fluorescence. Typically quenching poses a problem for non-instant spectroscopic methods, such as laser-induced fluorescence, but can also be used in producing biosensors. In certain aspects the fluorescence of a labeled aptamer that is not bound to its target is quenched, wherein upon binding to its target the fluorescence is recovered and can be detected. The labeled aptamer is complexed with a quenching moiety while absorbed onto the paper layer of a device as described herein. Once the aptamer binds its target the fluorescence is recovered. Target binding results in increased fluorescence.

In certain aspects the fluorescence of aptamers and probes can be quenched by graphene oxide, graphene and carbon nanoparticles. In certain aspects the aptamer/graphene oxide complex is adsorbed to a paper substrate or layer. Graphene oxide (GO) is a compound of carbon, oxygen, and hydrogen in variable ratios, obtained by treating graphite with strong oxidizers. Graphene oxide (GO) is an intermediate on the route to chemically derived graphene, and it is easily synthesized. Its chemical structure is heterogeneous and consists of both large areas of conjugated sp2-systems and various electronically isolated oxygen containing functionalities. GO can act as a quencher of fluorescence and is easily dispersible in water. In some instances the binding of the target results in desorption of the aptamer, which in turn results in an increase in fluorescence.

III. PATHOGENIC MICROBES

The emergence of 335 infectious diseases in the human population has been reported between 1940 and 2004, which has caused an extremely significant impact on global health and economies (Jones et al. (2008) *Nature*, 45: 990-93; Morens et al. (2004) *Nature*, 430: 242-49). Among various global infectious diseases, epidemic meningitis is one of most dangerous diseases. Epidemic meningitis is a severe and fast acting bacterial and/or viral infection of the brain and can become fatal as early as 24 hours after symptoms present. According to the World Health Organization, "Worldwide, without epidemics one million cases of bacterial meningitis are estimated to occur and 200,000 of these die annually . . . . Higher case-fatality rates (37-60%) have been reported in developing countries." (Castillo, *WHO Manual*, 2nd Edition, 2011). In addition, many case of meningitis occur in rural high-poverty areas, such as the "meningitis belt" of Africa where it remains an important and unresolved public health problem.

*Neisseria meningitides*, the etiologic agent of meningococcal disease, is a leading cause of morbidity and mortality in children and young adults worldwide (Goldacre et al. (2003) *BMJ*, 327: 596-97; Heyderman et al. (2004) *Archives of Disease in Childhood*, 89: 1064-68). *N. meningitides* is also the dominant etiologic agent in the meningitis belt according to bacteriologic and epidemiologic data over the past 30 years (LaForce et al. (2009) *Vaccine*, 27: Supplement 2, B13-B19).

Along with *Neisseria meningitidis* (*N. meningitidis*), *Streptococcus pneumoniae* (*S. pneumoniae*), and *Haemophilus influenzae* type B (Hib) are three most common pathogens that cause most of bacterial meningitis. As a medical emergency, immediate antibiotic therapy is imperative, which must not be postponed by diagnostic delays. In addition, identification of the exact bacteria causing the disease is vital because treatment and antibiotics differ for each type. Due to the high fatality rate and the damaging effect that can be caused by untreated meningitis, considering many cases of meningitis cases happed in rural high-poverty areas, a simple, low-cost, highly-sensitive and specific approach for immediate multiplexed bacterial meningitis diagnosis is in great need for subsequent treatment.

In one embodiment, the invention concerns rapid and accurate methods for detecting food-borne pathogens, including without limitation, parasites and their eggs, Noroviruses (Norwalk-like viruses), *Campylobacter* species, *Giardia lamblia, Salmonella, Shigella, Cryptosporidium parvum, Clostridium* species, *Toxoplasma gondii, Staphylococcus aureus*, Shiga toxin-producing *Escherichia coli* (STEC), *Yersinia enterocolitica, Bacillus cereus, Bacillus anthracis, Cyclospora cayetanensis, Listeria monocytogenes, Vibrio parahemolyticus* and *V. vulnificus*. The term "microorganism" or "microbe as used in this disclosure includes a virus, bacterium, fungi, parasite, or parasite's egg.

In certain aspects a pathogenic or potentially pathogenic microbe can be detected. A pathogenic microbe can be a virus, a bacteria, and/or a fungus. In certain aspects the device can be configured to detect a variety of microbes include viruses, bacteria, and fungi simultaneously. In certain aspects, a microbe includes a virus. The virus can be from the Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae family of viruses; and/or Parainfluenza, *B. pertussis*, Influenza, H5N1, Marburg, Ebola, Severe acute respiratory syndrome coronavirus, Yellow fever virus, Human respiratory syncytial virus, Hantavirus, or Vaccinia virus.

In yet a further aspect, the pathogenic or potentially pathogenic microbe can be a bacteria. A bacteria can be an intracellular, a gram positive, or a gram negative bacteria. In a further aspect, the bacteria includes, but is not limited to a *Escherichia*, a *Staphylococcus*, a *Bacillus*, a *Francisella*, or a *Yersinia* bacteria. In still a further aspect, the bacteria is *Bacillus anthracis*, *Yersinia pestis*, *Francisella tularensis*, *Pseudomonas aerugenosa*, or *Staphylococcus aureas*. In still a further aspect, a bacteria is a drug resistant bacteria, such as a multiple drug resistant *Staphylococcus aureas* (MRSA). Representative medically relevant Gram-negative bacilli include *Hemophilus influenzae*, *Klebsiella pneumoniae*, *Legionella pneumophila*, *Pseudomonas aeruginosa*, *Escherichia coli*, *Proteus mirabilis*, *Enterobacter cloacae*, *Serratia marcescens*, *Helicobacter pylori*, *Salmonella enteritidis*, and *Salmonella typhi*. Representative gram positive bacteria include, but are not limited to *Bacillus*, *Listeria*, *Staphylococcus*, *Streptococcus*, *Enterococcus*, *Actinobacteria* and *Clostridium Mycoplasma* that lack cell walls and cannot be Gram stained, including those bacteria that are derived from such forms.

In still another aspect, the pathogenic or potentially pathogenic microbe is a fungus, such as members of the family Aspergillus, Candida, Crytpococus, Histoplasma, Coccidioides, Blastomyces, Pneumocystis, or Zygomyces. In still further embodiments a fungus includes, but is not limited to *Aspergillus fumigatus*, *Candida albicans*, *Cryptococcus neoformans*, *Histoplasma capsulatum*, *Coccidioides immitis*, or *Pneumocystis carinii*. The family zygomycetes includes Basidiobolales (Basidiobolaceae), Dimargaritales (Dimargaritaceae), Endogonales (Endogonaceae), Entomophthorales (Ancylistaceae, Completoriaceae, Entomophthoraceae, Meristacraceae, Neozygitaceae), Kickxellales (Kickxellaceae), Mortierellales (Mortierellaceae), Mucorales, and Zoopagales.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

One-Step Detection

Simple One-Step Pathogen Detection Strategy in a PDMS/Paper Hybrid Microfluidic System.

FIG. 1 shows the main principle of the one-step pathogen detection biosensor using aptamer-functionalized GO in a microfluidic system. GO is a two-dimensional nanomaterial with extraordinary distance-dependent fluorescence quenching property, by means of π-stacking interactions between nucleotide bases and the GO sheet (Chang et al. *Anal. Chem.* 2010. 82:2341-46) thus allowing GO to serve as an excellent quencher to different fluorescence dyes (Zhu et al. *Adv. Mater.*, 2010, 22:3906-24). The fluorescence is quenched when fluorescence-labeled aptamers are adsorbed on the GO surface (Fluorescence 'OFF'). However, when a target is present, the aptamer will bind specifically to the target. The competitive binding between the target and the aptamer-GO, forces the cy3-labeled aptamer-GO structure to undergo a conformational alteration in response to interaction with the target, spontaneously liberating the aptamer from the GO surface, and thus resulting in the fluorescence recovery (Fluorescence 'ON'). In the absence of the target pathogen, no fluorescence restoration is detected.

Figures 2A, 2B:
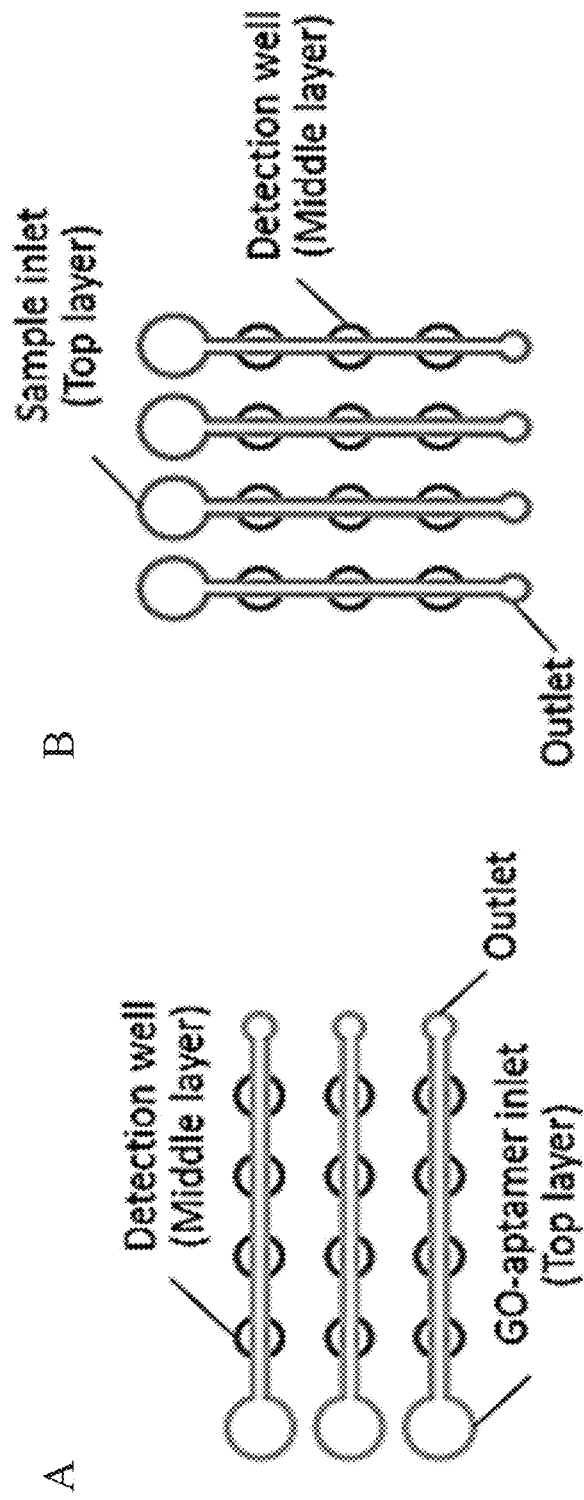
FIG. 2A-2B. Schematic to illustrate the protocol to introduce the GO-aptamer mixture (A) and samples (B) separately into detection wells by using two top PDMS films with orthogonally-orientated microchannels.

Instead of using complicated surface modification procedures for aptamer probe immobilization, a simple strategy is used to integrate the aptamer-functionalized GO biosensor in the microfluidic chip through the novel use of the porous chromatography paper as a simple 3D storage substrate for the GO-aptamer nano-biosensor in microwells. The GO-aptamer mixture is simply introduced into microwells through laterally oriented microchannels in a top PDMS film, as illustrated in FIG. 2A. It will be absorbed and stored in the small pieces of chromatography paper in microwells. The high surface-to-volume property of the porous paper improves reaction kinetics for rapid assays. Once the paper is dry, the device is ready to use. The pathogen test only needs the one-step loading of pathogen samples into detection microwells, even without the need of an additional washing step. Furthermore, this strategy takes cells directly as the detection target, without any complicated DNA treatment such as DNA extraction, amplification and purification. Therefore, this one-step 'Turn-on' mechanism offers simplicity and high sensitivity in pathogen detection.

Aptamer Concentration Optimization.

Figure 3:
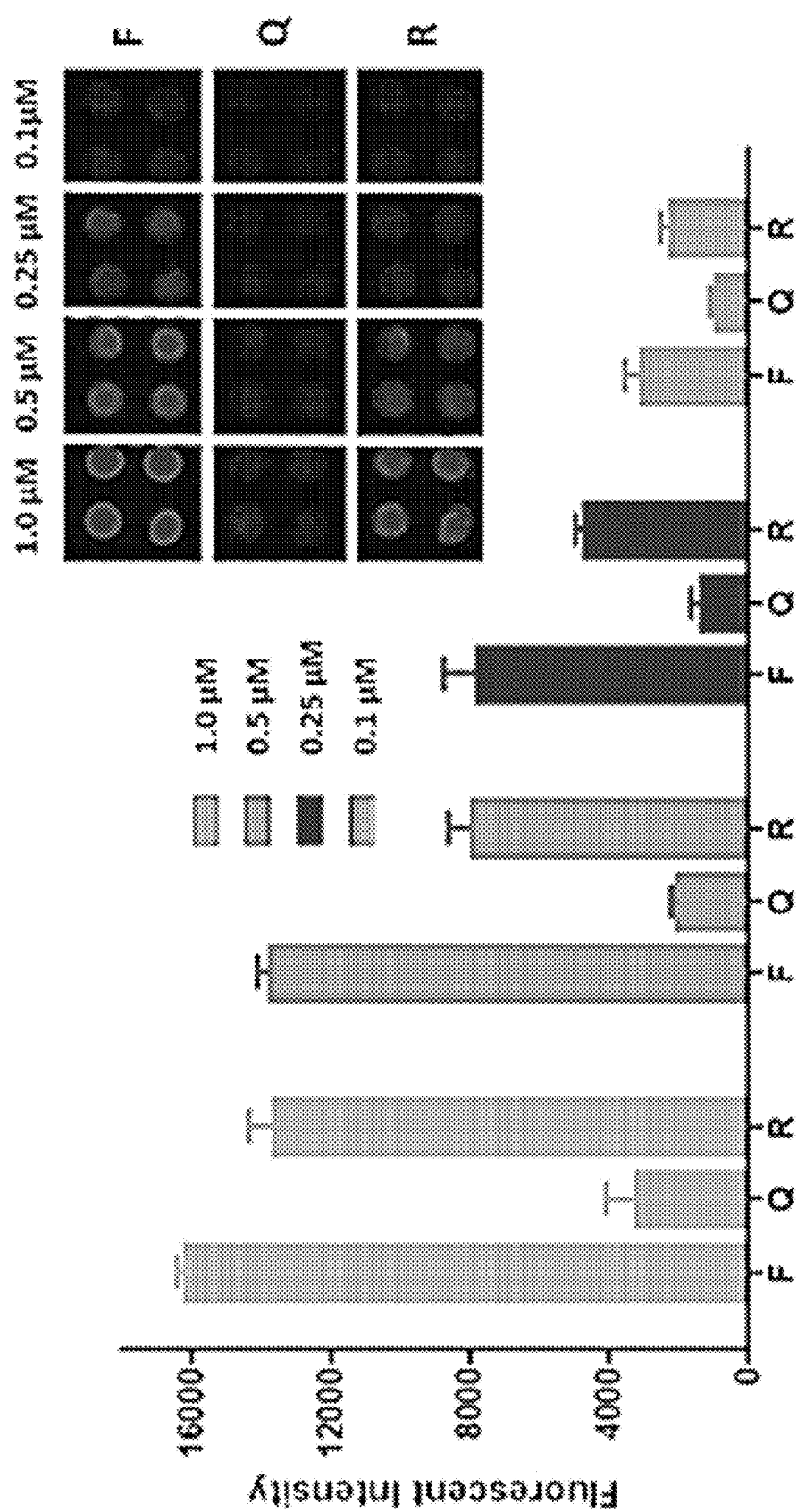
FIG. 3. Optimization of the aptamer concentration. The inset is a fluorescence image of different concentrations of the aptamer for *L. acidophilus* (150.0 cfu/mL) before quenching (F), after quenching (Q), and after fluorescence recovery (R).

Aptamer concentration affects fluorescence quenching and recovery. To optimize the aptamer concentration, four different concentrations of the fluorescently labeled aptamer for *L. acidophilus* (FALA (SEQ ID NO:3) ranging from 0.1 to 1.0 µM were tested. Different fluorescence responses of different concentrations of the aptamer before and after quenching and after recovering are shown in FIG. 3. It can be seen that when GO was mixed with the aptamer, the fluorescence of the aptamer was significantly quenched for all concentrations of the aptamer, and the fluorescence was restored due to the release of the fluorescent aptamer FALA from the GO surface, when 300.0 cfu/mL *L. acidophilus* was introduced. Given higher recovered fluorescence intensity and higher recovery rate (~85%) from 1.0 µM FALA, the aptamer concentration of 1.0 µM was chosen for subsequent experiments.

Quenching Time and Recovery Time.

Figure 4:
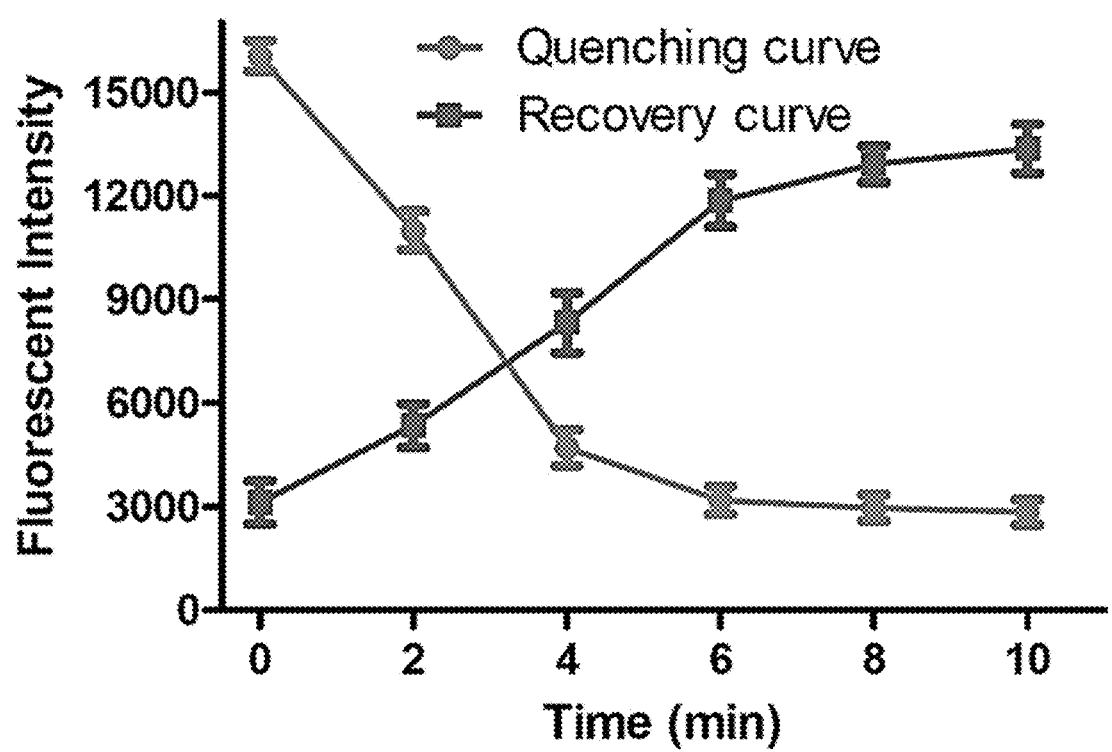
FIG. 4. Investigation of the quenching time and recovery time. *L. acidophilus*, 150.0 cfu/mL; the aptamer FALA, 1.0 µM.

To achieve high detection sensitivity, low quenched fluorescence (i.e., low background) and higher recovered fluorescence intensities are desired. Different incubation times of 2, 4, 6, 8, and 10 min for fluorescence quenching and recovery were conducted and compared. As shown in FIG. 4, minimal quenched fluorescence can be achieved within ~10 min, whereas maximal recovered fluorescence can be obtained within ~8 min. In consequence, 10 min and 8 min were used as the quenching time and recovery time, respectively. Therefore, once a ready-to-use devices is prepared (i.e., after GO-aptamer biosensor preparation in the chip), the one-step assay in such a microfluidic system takes only ~10 min to complete, providing a simple method for fast pathogen detection.

Calibration Curve and Limit of Detection (LOD) for *L. acidophilus*.

Figures 5A, 5B:
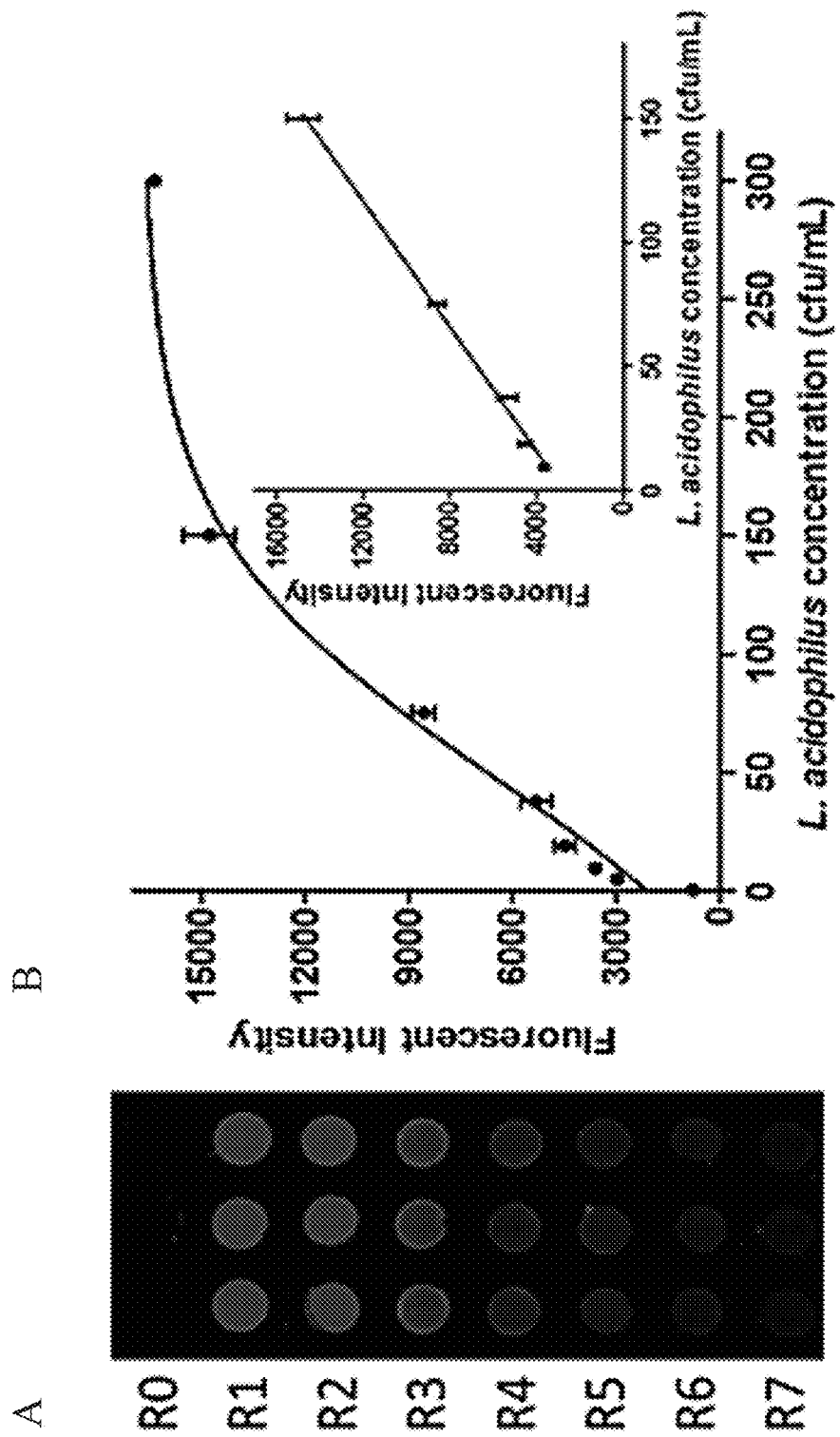
FIG. 5A-5B. Detection of various concentrations of *L. acidophilus*. (A) A fluorescent image of a 3×8 well array in the detection of *L. acidophilus*. Rows 0-8 (R0-R8) represent different concentrations of *L. acidophilus*. R0: 0 cfu/mL; R1: 300.0 cfu/mL; R2: 150.0 cfu/mL; R3: 75.0 cfu/mL; R4: 37.5 cfu/mL; R5: 18.8 cfu/mL; R6: 9.4 cfu/mL; and R7: 4.7 cfu/mL. (B) Calibration plot of the recovered fluorescence versus the concentration of *L. acidophilus* from 0-300.0 cfu/mL (N=8). Table inset shows linear calibration curve for the detection of *L. acidophilus* from 9.4-150.0 cfu/mL with a correlation coefficient ($R^2$) of 0.997.

Under optimized conditions, various concentrations of *L. acidophilus* were tested on the chip. FIG. 5 shows different recovered fluorescence intensities versus various concentrations of *L. acidophilus* from 0-300 cfu/mL. The control experiment (R0 in FIG. 5A) shows low fluorescence background when the test target was absent. With the concentration increase of the bacteria, higher fluorescence intensity was recovered. As shown in FIG. 5B, the linear range of the calibration curve is from 9.4 to 150.0 cfu/mL with a correlation coefficient of 99.7%. However, when the concentration of *L. acidophilus* increases above 150.0 cfu/mL, the correlation becomes non-linear, indicated by a plateau in the curve. The LOD for the detection of *L. acidophilus* was calculated to be ~11.0 cfu/mL, based on the usual 3σ. Multiple detection wells on the chip made it possible to complete the test of eight different concentrations of *L. acidophilus* in one assay within ~10 min, using the ready-to-use microfluidic system. The successful detection of *L. acidophilus* enabled us to explore the analysis of more complex pathogen systems.

Multiplexed Pathogen Detection.

In many cases of real samples, multiple pathogens could co-exist. Multiplexed pathogen detection provides not only convenience from one assay, but also rich pathogen information from one assay. Therefore, on the basis of the one-step detection of *L. acidophilus*, the capacity of the approach in detecting more complex pathogen systems (multiplexed pathogen detection) was investigated. Two common bacterial food-borne pathogens, *S. aureus* and *S. enterica* were choosen. Both can cause a range of illnesses, from minor skin infections to life-threatening diseases (Bost et al. *Infect. Immun.*, 2000, 68:5075-83; Swartz, *Clin. Infect. Dis.* 2002. 34 Suppl 3:S111-22).

Figure 6:
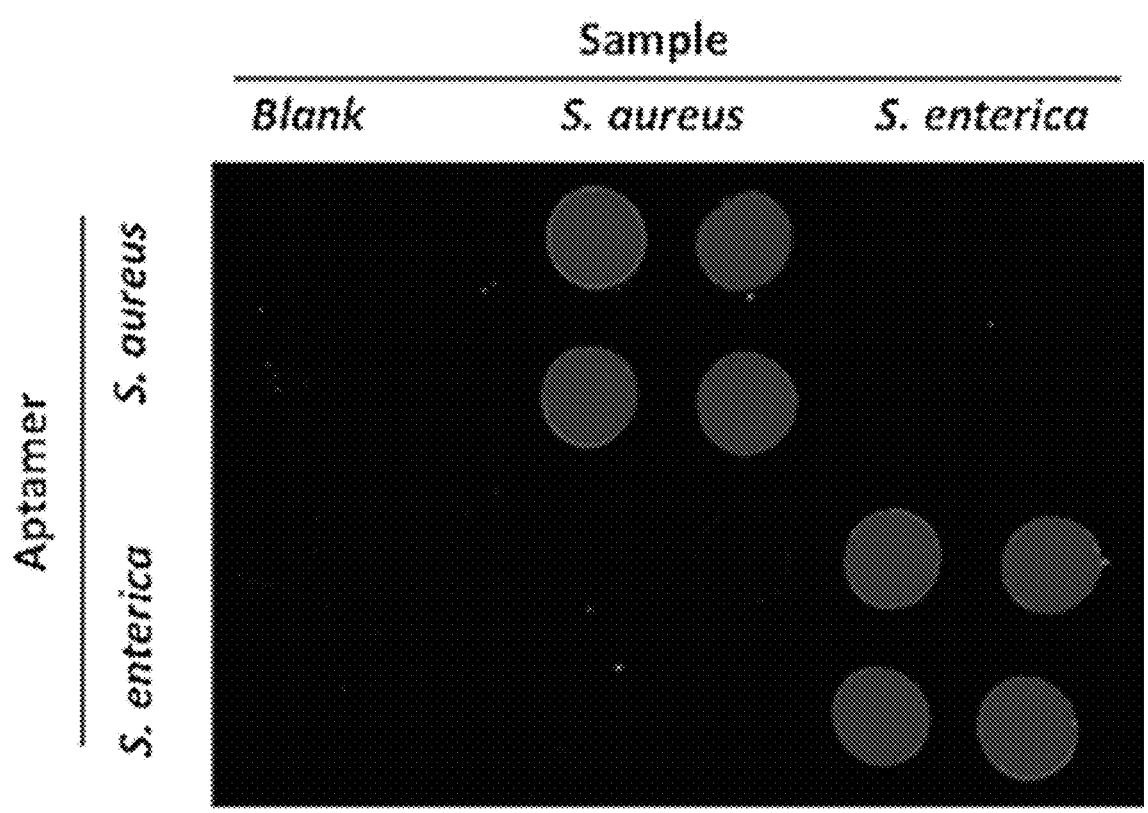
FIG. 6. Cross reaction investigation by testing *S. aureus* ($10^6$ cfu/mL) and *S enterica* (1375 cfu/mL) with their corresponding and non-corresponding aptamers. Specific aptamers for *S. aureus* and *S. enterica* (i.e. FASA (SEQ ID NO:1) and FASE (SEQ ID NO:2) were first immobilized in detection wells of the top two and the bottom two rows, respectively. Blank and pathogen samples were separately introduced from vertically-oriented channels.

To validate the selectivity of the approach for *S. aureus* and *S. enterica*, and avoid interference from each other, cross reactivity was studied by testing these two pathogens with their corresponding and non-corresponding aptamers separately. As shown in FIG. 6, the top two rows of detection wells were prepared with the FASA-functionalized GO biosensor for *S. aureus* detection from laterally-orientated microchannels, while the bottom two rows of detection wells were prepared with the FASE-functionalized GO biosensor for *S. enterica* detection. When the blank sample and *S. aureus* were introduced from the left two and the middle two columns separately, only the four top middle microwells (rather than the bottom middle four microwells) showed significant fluorescence recovery, indicating the high specificity of the GO-functionalized FASA biosensor and no interference from *S. enterica* for the detection of *S. aureus*. Similarly, when *S. enterica* was introduced from the right two columns, only the right bottom four microwells showed strong fluorescence recovery, indicating no cross reaction observed from *S. aureus* for the detection of *S. enterica* as well.

Figure 7A:
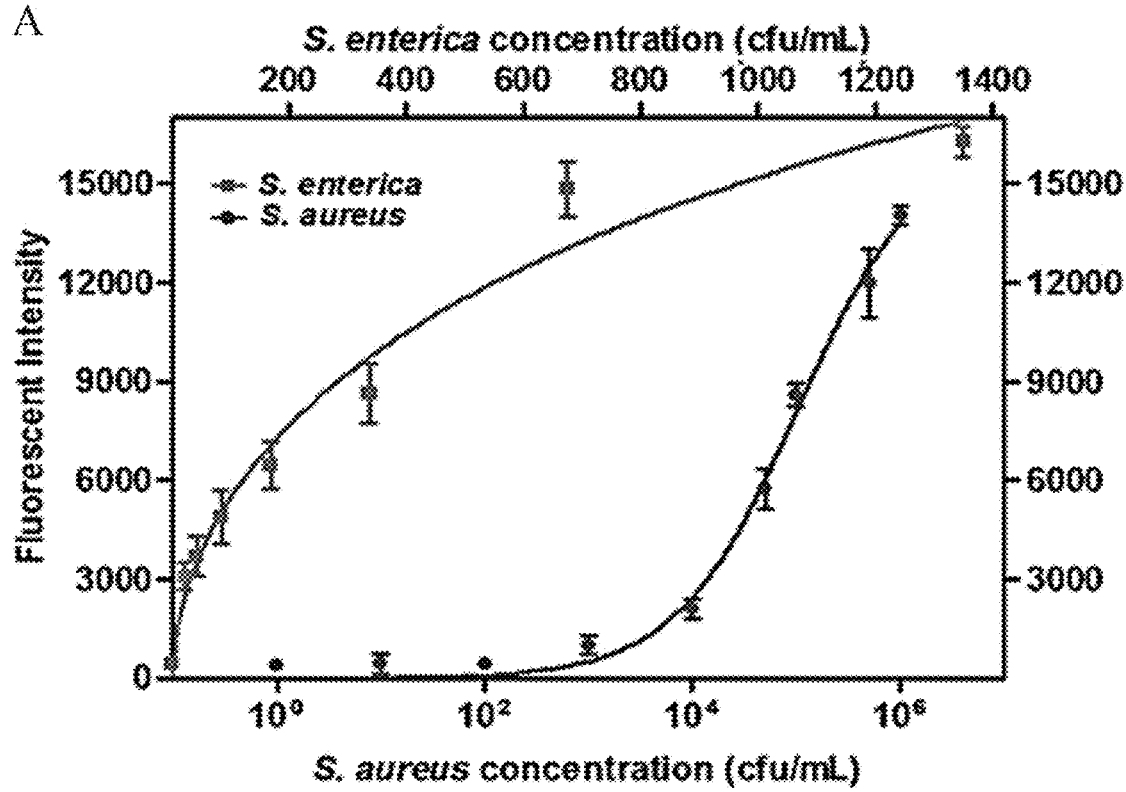
FIG. 7A-7B. One-step simultaneous detection of *S. enterica* and *S. aureus*. (A) Calibration plots of the fluorescence intensity versus the pathogen concentration in the simultaneous detection of *S. enterica* and *S. aureus*. (B) Linear calibration curves for the detection of *S. enterica* and *S. aureus*, with correlation coefficients ($R^2$) for *S. enterica* and *S. aureus* were 0.995 and 0.993, respectively.
Figure 7B:
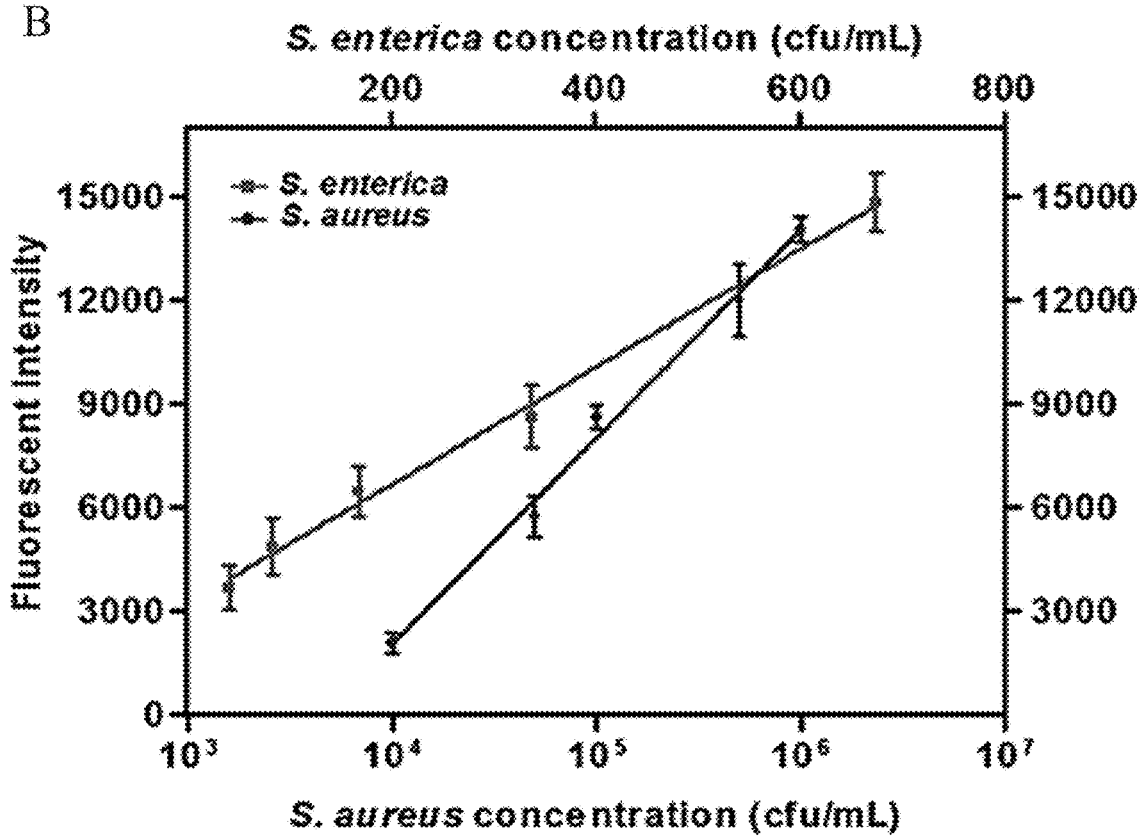

After ruling out cross reaction from each other, simultaneous detection of *S. enterica* from 0-1375 cfu/mL and *S. aureus* from 0-$10^6$ cfu/mL was performed using the microfluidic biochip integrated with aptamer-functionalized GO biosensors for *S. enterica* and *S. aureus*. The calibration curves for the simultaneous detection of *S. enterica* and *S. aureus* were generated by plotting the fluorescent intensity against the pathogen concentration, as shown in FIG. 7. The two curves in FIG. 7A show quite different shapes. The biosensors seem to be more sensitive to low concentrations than high concentrations of *S. enterica*, whereas the biosensors show the opposite phenomena in the detection range for *S. aureus*. This might be due to the different pathogen capture properties of their aptamers. The linear ranges of the calibration curves were 42.2-675.0 cfu/mL for *S. enterica* and $10^4$-$10^6$ cfu/mL for *S. aureus*. Based on the usual 3σ, the LODs for *S. enterica* and *S. aureus* were approximated to be 61.0 cfu/mL and 800.0 cfu/mL, respectively. This indicates similar performance of the microfluidic approach in this aspect as other aptamer-based detection methods for *S. enterica* and *S. aureus* reported previously (Joshi et al., *Mol. Cell Probe*, 2009, 23:20-28; Zelada-Guillen et al. *Biosensors & Bioelectronics*, 2012, 31:226-32). Therefore, this microfluidic approach is not only simple (e.g. one-step), but also provides high-density pathogen information from its multiplexed capacity.

Sample Test.

Spiked samples were employed for assessing the accuracy of the presented method. *S. enterica* at concentrations of 84.4 and 168.8 cfu/mL and *S. aureus* at concentrations of 50000.0 and 500000.0 cfu/mL were spiked and tested by the microfluidic system. The test results are listed in Table 2. With 84.4 and 168.8 cfu/mL *S. enterica* spiked, 78.4 and 162.7 cfu/mL *S. enterica* were measured, with the Coefficients of Variation (CV) of 7.3% and 5.5%, respectively. With the addition of 50000.0 and 500000.0 cfu/mL *S. aureus*, 51668.4 and 539371.2 cfu/mL *S. aureus* were measured, with the Coefficients of Variation (CV) of 7.25% and 9.45%, respectively. The percent recovery for all spiked samples falls into the range between 92.9-107.8%, denoting fairly high accuracy of the approach.

TABLE 2

Test results of spiked samples (n = 10)

| Pathogen | Spiked cfu/mL | Average measured cfu/mL | Coefficient of Variation | Percent Recovery |
|---|---|---|---|---|
| *S. enterica* | 84.4 | 78.4 | 7.3% | 92.9% |
| | 168.8 | 162.7 | 5.5% | 96.4% |
| *S. aureus* | 50000.0 | 51668.4 | 7.3% | 103.3% |
| | 500000.0 | 539371.2 | 9.5% | 107.8% |

Chemicals and Materials.

The sequences of the three aptamers (Hamula et al., *Anal Chem.*, 2008, 80:7812-19; Joshi et al., *Mol. Cell Probe*, 2009, 23:20-28; Cao et al., *Nucleic Acids Res*, 2009, 37:4621-28) used in this paper are: *Lactobacillus acidophilus*—FALA (cy3-ATCCGTCACACCTGCTCTACG-GCGCTCCCAACAGGCCTCTCCTTACGGCATATTATG GTGTTGGCTCCCGTAT (SEQ ID NO:3)), *Staphylococcus aureus*—FASA (cy3-GCAATGGTACGGTACTTCCTCG-GCACGTTCTCAGTAGCGCTCGCTGGTCATCCCACA GCTACGTCAAAAGTGCACGCTACTTTGCTAA (SEQ ID NO:1)), and *Salmonella enterica*—FASE (cy3-TATG-GCGGCGTCACCCGACGGGGACTTGACATTAT-GACAG (SEQ ID NO:2)). The polynucleotides were purchased from Integrated DNA Technologies, (Coralville, Iowa). Graphene oxide (GO) was purchased from Graphene Laboratories. Polydimethylsiloxane was obtained from Dow Corning (Midland, Mich.). Whatman chromatography paper and all other mentioned chemicals and solvents were purchased from Sigma (St. Louis, Mo.) and used without further purification unless stated otherwise. Unless otherwise noted, all solutions were prepared with ultrapure water (Milli-Q water, 18.2 MΩ·cm) from a Millipore Milli-Q system (Bedford, Mass.).

Microorganism Culture.

The *Lactobacillus acidophilus* (*L. acidophilus*, ATCC#4356), *Staphylococcus aureus* (*S. aureus*, ATCC#29213) and *Salmonella enterica* (*S. enterica*, ATCC#14028) were obtained from the American Type Culture Collection (ATCC, Rockville, Md.). *L. acidophilus* was grown under anaerobic conditions at 37° C. for 48 h in Lactobacilli MRS Broth (BD, Franklin Lakes, N.J.) according to ATCC instruction. *S. enterica* and *S. aureus* were grown in McConkeys agar and 5% sheep blood agar (BD, Franklin Lakes, N.J.), respectively, and incubated at 37° C. for 24 h. Colonies on plates were counted to determine the number of colony-forming units per milliliter (cfu/mL). Cells were pelleted at 1800×g at 4° C. and then washed twice with 1×binding buffer (50 mM Tris-HCl, pH 7.4 with 5 mM KCl, 100 mM NaCl, and 1.0 mM $MgCl_2$) at room temperature (RT). Cells were finally suspended in 1×binding buffer before use.

Microfluidic Chip Design and Fabrication.

The microfluidic system includes two PDMS layers and one glass plate as the bottom layer, for example see FIG. 1. The top PDMS layer is designed for reagent delivery. It has 32 micro-channels and inlet reservoirs and one shared waste reservoir in the center. The middle PDMS layer (also called incubation layer) has four 3×8 microwell arrays, where incubation and detection were carried out. The total 96 wells can allow for 96 tests from one assay, thus providing high-throughput analysis. A piece of circular chromatography paper was punched into small round pieces, placed inside each microwell, and served as the substrate for adsorbing the aptamer-GO mixture in subsequent steps.

All PDMS films were prepared following standard soft lithography procedures (Xia and Whitesides, *Annu. Rev. Mater. Sci.*, 1998, 28:153-84). Briefly, the liquid PDMS base and the curing agent from the Dow Corning Sylgard 184 kit (Corning, N.Y.) were mixed typically at a ratio of 10:1 (m/m). After degassing, the liquid pre-polymer mixture poured in a petri dish was placed in an oven and incubated overnight at 60° C. Different from commonly used PDMS moulding to create micro channels, channels were created on the top PDMS film using a laser cutter (Epilog Zing 16, Golden, Colo.). Inlet and outlet reservoirs in the top PDMS layer, and microwells in the middle PDMS layer were formed using biopsy punches. After a 30 second exposure to an oxidizing air plasma (Ithaca, N.Y.), PDMS films and the glass plate were face-to-face sandwiched to bond irreversibly.

Assay Procedures.

GO was diluted in Milli-Q water and then mixed with the fluorescent aptamer solution at a final optimal concentration. The GO-Aptamer mixture was incubated for a period of time to quench the fluorescence of the aptamer significantly, and the optimal quenching time was investigated by introducing GO aptamer mixture into detection wells on the chip. Two separate PDMS films with orthogonally-oriented microchannels were used to deliver the GO-aptamer mixture and samples subsequently into detection wells such that it avoided cumbersome pipetting and the use of expensive robots in loading reagents into the 96 wells in the device. First, an aliquot of 10 μL aptamer-GO mixture was loaded in the aptamer-GO inlets of the top 'laterally-orientated' PDMS microchannels and delivered to the different detection wells by capillary action through microchannels (FIG. 2A). The chromatography paper inside the wells absorbed the aptamer-GO mixture, and was left to dry at RT after the top PDMS layer was peeled away. The fluorescence intensity of each well was recorded prior to the addition of the corresponding target. Hence the aptamer-functionalized grapheme oxide biosensors for the subsequent assay were prepared on the chip. Second, another top PDMS film with orthogonal channels to the previous aptamer-GO introduction channels (FIG. 2B) was bound with the middle PDMS layer. An aliquot of 30 μL of the test sample was loaded in each sample inlet reservoir to introduce the sample to the different detection wells. After incubation for a period of time of 8 min at RT, the device was scanned by a Nikon Ti-E Fluorescence Microscope that was equipped with a motorized stage and a cooled CCD camera to measure the fluorescence intensities, using appropriate Cy3 optical filters.

*L. acidophilus* prepared in 1×binding buffer was introduced into the microchannels to establish the aptamer based microfluidic system for further infectious pathogen detection. The aptamer concentration, quenching time and recovery time were also investigated to obtain optimal assay conditions. The optimized conditions were further applied to the multiplexed detection of two infectious pathogens using *S. aureus* and *S. enterica* as representative bacteria.

Example 2

Microfluidic Spinchip

A. Chemicals and Materials

Table 3 lists the sequence information of the LAMP primers and probes for *N. meningitidis* (McKenna et al., *Diagnostic Microbiology and Infectious Disease*, 2011, 69(2):137-44; Mothershed et al., *Journal of clinical microbiology*, 2004, 42(1):320-8) and *S. pneumoniae* (Kim et al., *PLoS ONE*, 2012, 7(8):e42954; Zuiderwijk et al., *Clinical biochemistry*, 2003, 36(5):401-3), as well as the negative control probe (NC1) (Zuiderwijk et al., *Clinical biochemistry*, 2003, 36(5):401-3), which were all purchased from Integrated DNA Technologies. All of the probes are labeled with Cy3 at the 5' end.

LAMP DNA amplification kits were purchased from Eiken Co. Ltd., Japan. DNA isolation kits and LAMP products purification kits were purchased from Qiagen (Valencia, Calif.). The LAMP reaction mixture contained 20 mM Tris-HCl (pH 8.8), 10 mM KCl, 8 mM $MgSO_4$, 10 mM $(NH_4)_2SO_4$, 0.1% Tween 20, 0.8 M Betaine, 0.5 mM $MnCl_2$, 1.4 mM dNTPs, 8U Bst Polymerase, 1.6 μM each of the inner primer (FIP/BIP), 0.2 μM each of the outer primer (F3/B3), 0.4 μM each of the loop primer (LF/LB).

Artificial cerebrospinal fluid (ACSF) was prepared according to a published protocol (Artificial cerebrospinal fluid (ACSF). *Cold Spring Harbor Protocols*, Sep. 1, 2011, 2011(9):pdb.rec065730.), which contained 119 mM NaCl, 26.2 mM $NaHCO_3$, 2.5 mM KCl, 1 mM $NaH_2PO_4$, 1.3 mM $MgCl_2$, 10 mM glucose. The ACSF solution was bubbled with 5% $CO_2$/95% $O_2$ for 10-15 min, before adding $CaCl_2$ to reach a final concentration of 2.5 mM $CaCl_2$. Then the prepared ACSF solution was filtered with a 0.20 μm filter apparatus, and stored at 4° C. for use. Bacteria lysis buffer contained 50 mM Tris buffer (pH 7.5), 4 M urea and 0.1% triton.

GO and Whatman chromatography paper were obtained from Graphene Laboratories (Calverton, N.Y.) and Sigma (St. Louis, Mo.), respectively. Poly(methyl methacrylate) (PMMA) was purchased from McMaster-Carr (Los Angeles, Calif.). All other mentioned chemicals were purchased from Sigma (St. Louis, Mo.) and used without further purification, unless otherwise noted. Unless stated otherwise, all solutions were prepared with ultrapure Milli-Q water (18.2 MΩ cm) from a Millipore Milli-Q system (Bedford, Mass.).

TABLE 3

Sequence information of LAMP primers and
probes for N. meningitidis and S. pneumonia,
and the negative control (NC1) probe
(McKenna et al., Diagnostic Microbiology and
Infectious Disease, 2011, 69(2):137-44;
Kim et al., PLoS ONE, 2012, 7(8):e42954;
Mothershed et al., Journal of clinical
microbiology, 2004, 42(1):320-8; Zuiderwijk
et al., Clinical biochemistry, 2003, 36(5):
401-3; Chen et al., Journal of clinical
microbiology, 2011,
49(4):1653-6).

| LAMP Primer | Sequences (5'-3') | No. of bases |
|---|---|---|
| *N. meningitidis* ctrA LAMP primer sequences and the probe sequences | | |
| FIP | CAAACACACCACGCGCATCAGATCTGAAGC CATTGGCCGTA (SEQ ID NO: 4) | 41 |
| BIP | TGTTCCGCTATACGCCATTGGTACTGCCAT AACCTTGAGCAA (SEQ ID NO: 5) | 42 |
| F3 | AGC(C/T)AGAGGCTTATCGCTT (SEQ ID NO: 6) | 19 |
| B3 | ATACCGTTGGAATCTCTGCC (SEQ ID NO: 7) | 20 |
| FL | CGATCTTGCAAACCGCCC (SEQ ID NO: 8) | 18 |
| BL | GCAGAACGTCAGGATAAATGGA (SEQ ID NO: 9) | 22 |
| Probe | AACCTTGAGCAATCCATTTATCCTGACGTT CT (SEQ ID NO: 10) | 32 |
| *S. pneumoniae* lytA LAMP primer sequences and the probe sequences | | |
| FIP | CCGCCAGTGATAATCCGCTTCACACTCAAC TGGGAATCCGC (SEQ ID NO: 11) | 41 |
| BIP | TCTCGCACATTGTTGGGAACGGCCAGGCAC CATTATCAACAGG (SEQ ID NO: 12) | 43 |
| F3 | GCGTGCAACCATATAGGCAA (SEQ ID NO: 13) | 20 |
| B3 | AGCATTCCAACCGCC (SEQ ID NO: 14) | 15 |
| BL | TGCATCATGCAGGTAGGA (SEQ ID NO: 15) | 18 |
| Probe | GCGGATTCCCAGTTGAGTGTGCGTGTAC (SEQ ID NO: 16) | 28 |
| NC1 (Influenza A) probe sequences | | |
| Probe | TGCAGTCCTCGCTCACTGGGCACG (SEQ ID NO: 17) | 24 |

Microorganism Culture and DNA Preparation.

The *N. meningitidis* (ATCC 13098) and *S. pneumoniae* (ATCC 49619) were obtained from American Type Culture Collection (ATCC, Rockville, Md.). *N. meingitidis* was grown on chocolate II agar supplemented with hemoglobin and IsoVitalex plates (BD, Sparks, Md.). *S. pneumoniae* was grown in TSA II agar plates supplemented with 5% sheep blood (BD, Sparks, Md.). All the microorganisms were incubated at 37° C. for 48 h in an aerobic environment with 5% $CO_2$. DNA isolation and LAMP products purification procedures were followed by the protocol from the manufacturer.

Microfluidic SpinChip Design and Fabrication.

Figures 10A, 10B, 10C:
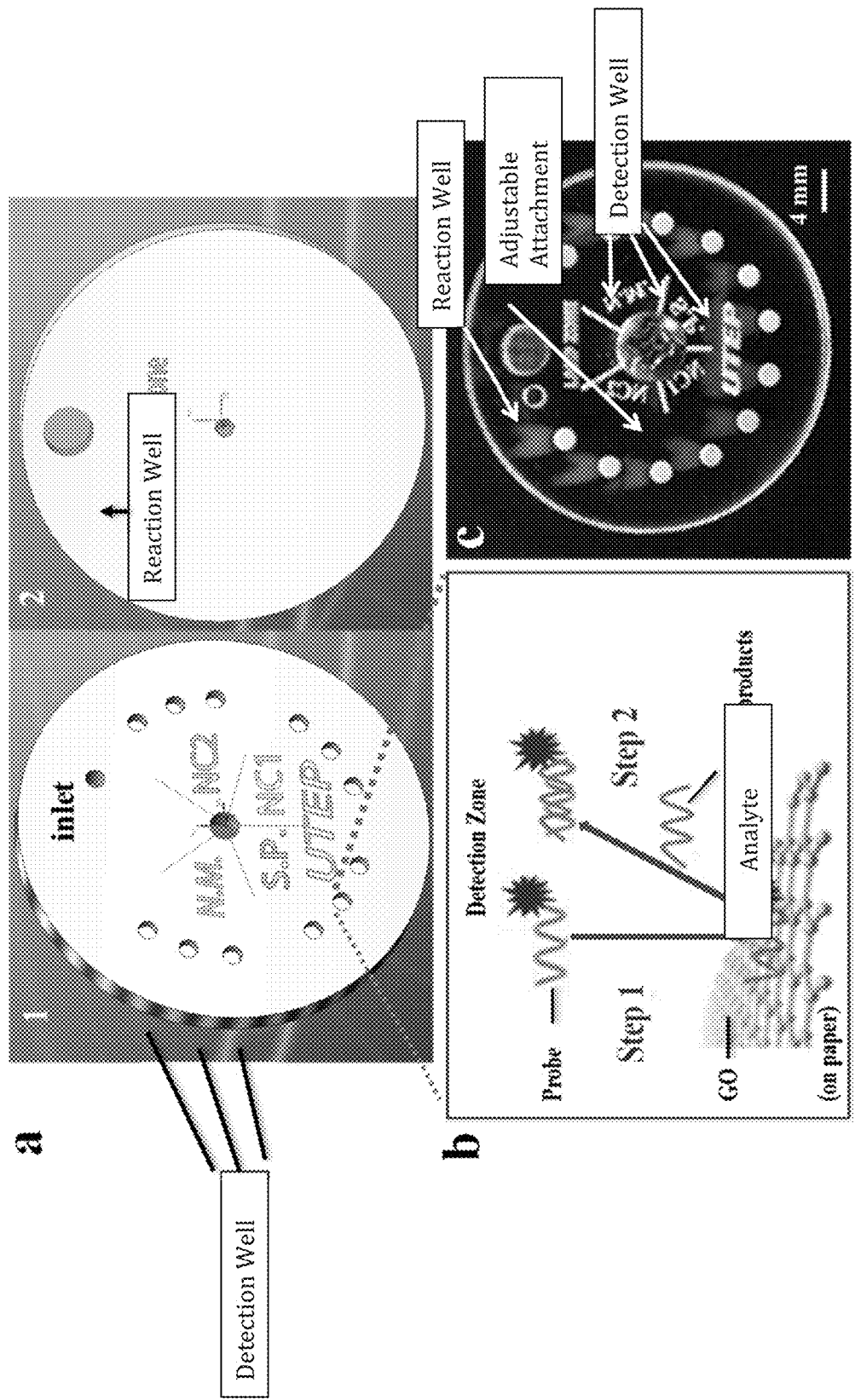
FIG. 10A-10C. (a) Schematic of the PMMA/paper hybrid microfluidic rotary chip (Spinchip) for multiplexed bacterial meningitis diagnosis. (b) Illustration of the detection principle based on the interaction among GO, probe and target LAMP products. Step 1: when the cy3 fluorescence labeled probe is adsorbed on the GO surface, its fluorescence is quenched. Step 2: when the target LAMP products are present, they induce the probe to be liberated from GO and thereby recovers its fluorescence for detection. (c) A photograph of the PMMA/paper hybrid microfluidic SpinChip.

As shown in FIG. 10, the microfluidic SpinChip has two plates tightened with a screw in a center. The bottom plate (FIG. 10A-2) that contains a LAMP zone. The top plate (FIG. 10A-1) contains 12 detection zones with a paper disk placed inside, in which GO nanosensors functionalized with Cy3-labeled probes are preloaded. The detection zones were divided into 4 areas, which were used for *N. meningitidis* and *S. pneumoniae* detection (N.M. and S.P.) with their corresponding probes, as well as 2 negative controls (NC1 and NC2). NC1 was preloaded with a non-target probe, Influenza A probe, as a negative control; No probe was preloaded for NC2. In addition, there was an inlet in the top plate, where samples can be introduced into the LAMP zone on the bottom plate.

The fabrication of hybrid microfluidic SpinChips is fast, simple and it is easy to operate. All the LAMP zone, detection zones and the chromatography paper disks were directly cut by a laser cutter (Epilog Zing 16, Golden, Colo.) within a few minutes. The bottom plate with LAMP zone was exposed in an oxidizing air Plasma cleaner (Ithaca, N.Y.) for 30 seconds, making the LAMP zone hydrophilic. A chromatography paper was tightly placed inside each detection zone as a 3D storage substrate for the GO nano-biosensors. The chromatography paper inside the detection zones absorbed GO and probe solutions by capillary effect. First, 0.8 μL 0.04 mg/mL GO was added into each detection zone. After it became dry in 5 minutes at room temperature, 0.8 μL probe solution was then added into each detection zone and was left to dry at room temperature in another 5 minutes. The two plates were then tightened together with a screw in the center of both plates. Then, the hybrid microfluidic SpinChip becomes ready to use.

Assay Procedures.

The LAMP reaction mix that was prepared in a biosafety cabinet was introduced to the LAMP zone from the inlet of microfluidic SpinChip, followed by covering the LAMP zone by rotating the top plate of the SpinChip and screwing the two plates tightly (FIG. 10C). After that, the SpinChip was placed on a heating film at 63° C. for 45 minutes for LAMP reaction. The fluidic path of the SpinChip is connected only when the top and bottom plate are aligned in a specific configuration. Therefore, after the LAMP reaction, the SpinChip was reversed and the bottom plate was rotated slowly so the complementary patterns of zones in both plates overlap, exposing the sample-containing LAMP zone of the bottom plate to the probes-containing detection zones of the top plate. After incubation for 15 min at room temperature, the SpinChip was scanned by a Nikon Fluorescence Microscope (Melville, N.Y.) to measure the fluorescence intensity, using appropriate Cy3 optical filters.

DNA Probe Concentration Optimization.

Figures 11A, 11B:
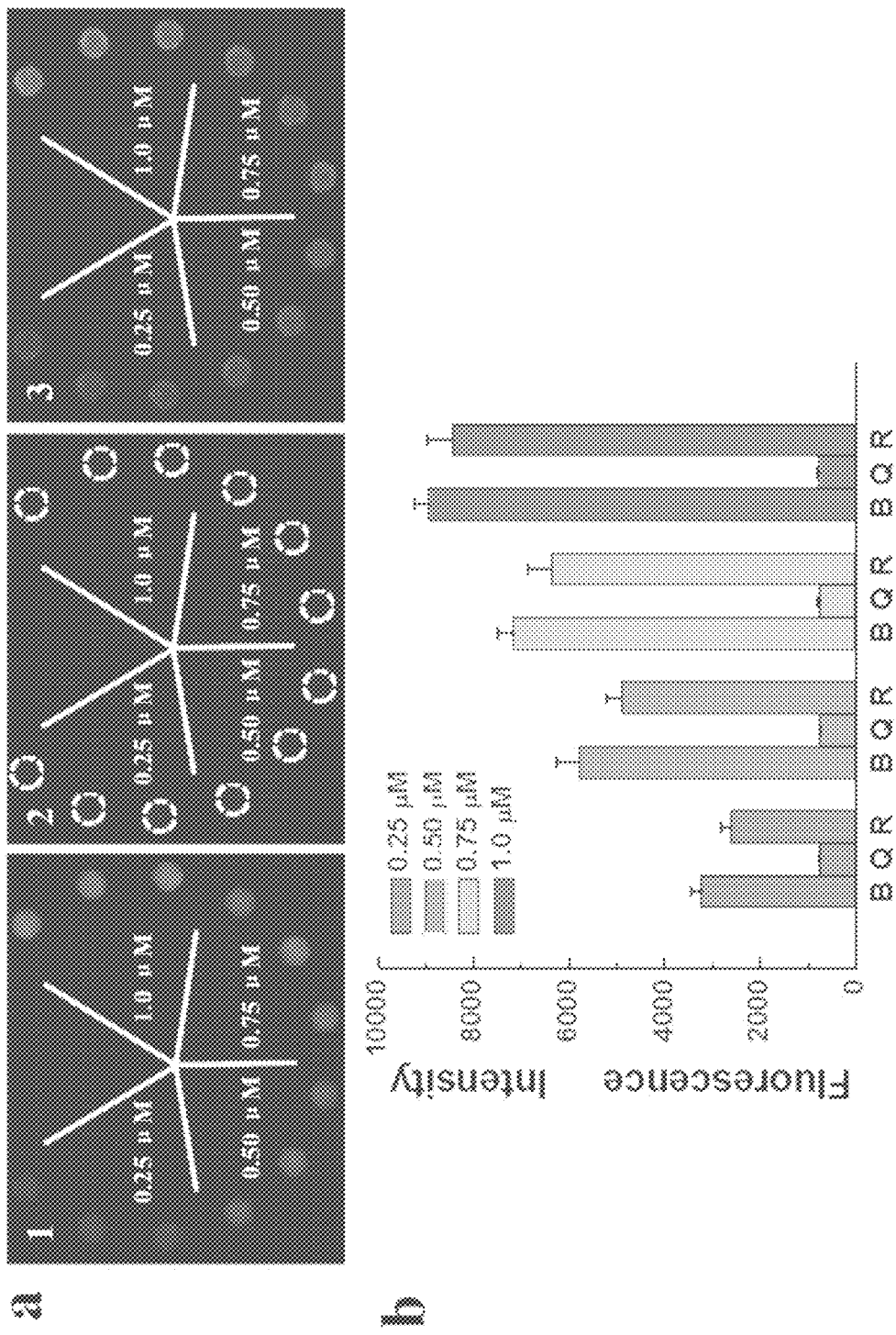
FIG. 11A-11B. Optimization of the probe concentration. Fluorescence images (a) and the corresponding fluorescence intensity (b) of different concentrations of the probe for *N. meingitidis* LAMP products (800 ng/µL) before quenching (a-1, B), after quenching (a-2, Q), and after fluorescence recovery (a-3, R).

To optimize the probe concentration, fluorescence images were obtained (FIG. 11A) and the corresponding fluorescence intensities (FIG. 11B) of different concentrations (0.25 μM, 0.50 μM, 0.75 μM and 1.0 μM) of the DNA probe for *N. meingitidis* LAMP products (800 ng/μL) before fluorescence quenching (FIG. 11A-1), after quenching (FIG. 11A-2), and after recovery (FIG. 11A-3). The highest fluorescence intensity after recovery and highest recovery rate (~94%) were observed under the probe concentration of 1.0 μM. Therefore, 1.0 μM probe concentration was used for the subsequent assays.

Specificity Detection.

Figures 12A, 12B:
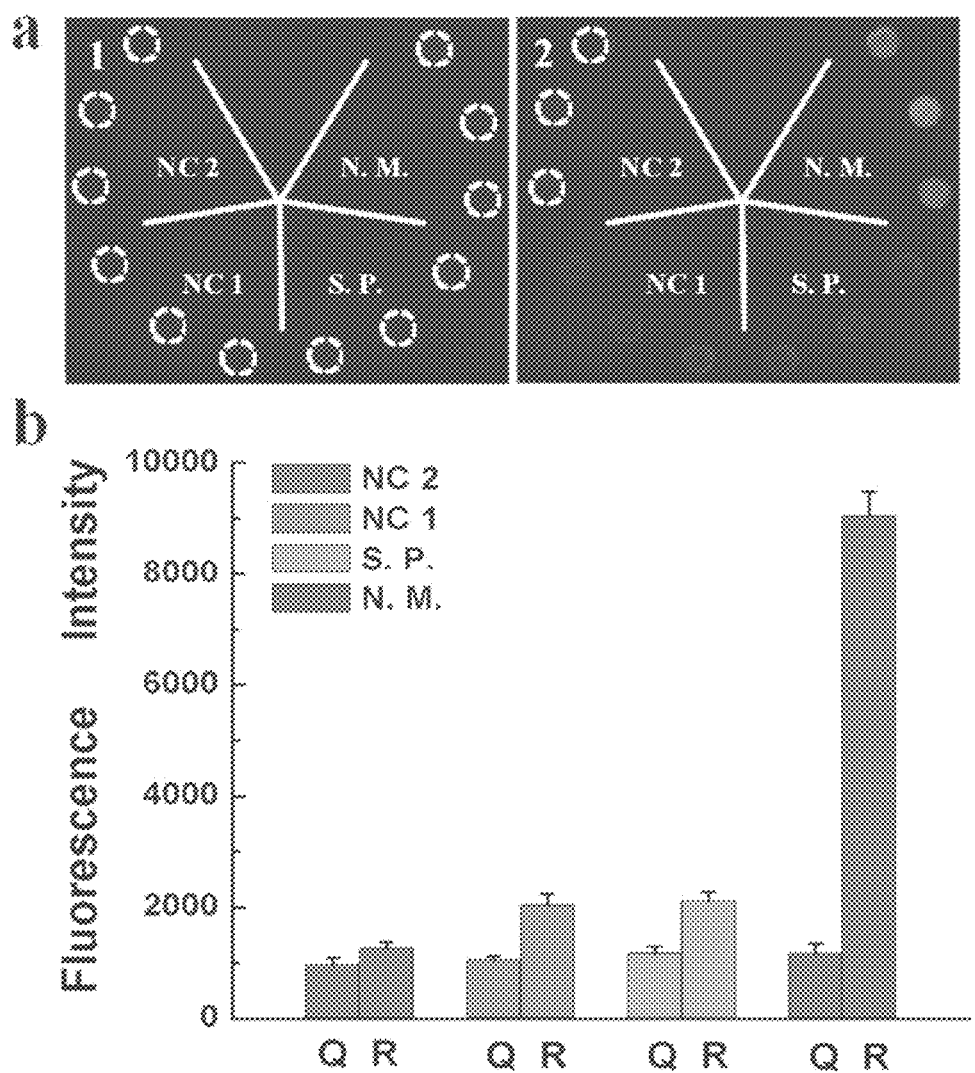
FIG. 12A-12B. Specificity detection by testing a *N. meningitidis* DNA sample with its corresponding and non-corresponding probes. (a) Microscope images of nano-biosensors after quenching (a-1) and after recovery (a-2) with amplified *N. menigitidis* DNA samples. (b) Fluorescence intensities of nano-biosensors after quenching (Q) and after recovery (R) with amplified *N. menigitidis* DNA sample. Specific probe for *N. meningitidis*, *S. pneumoniae* and NC1 were first immobilized in LAMP detection zones. (*N. meningitidis* LAMP products: 800 ng/µL).
Figures 13A, 13B:
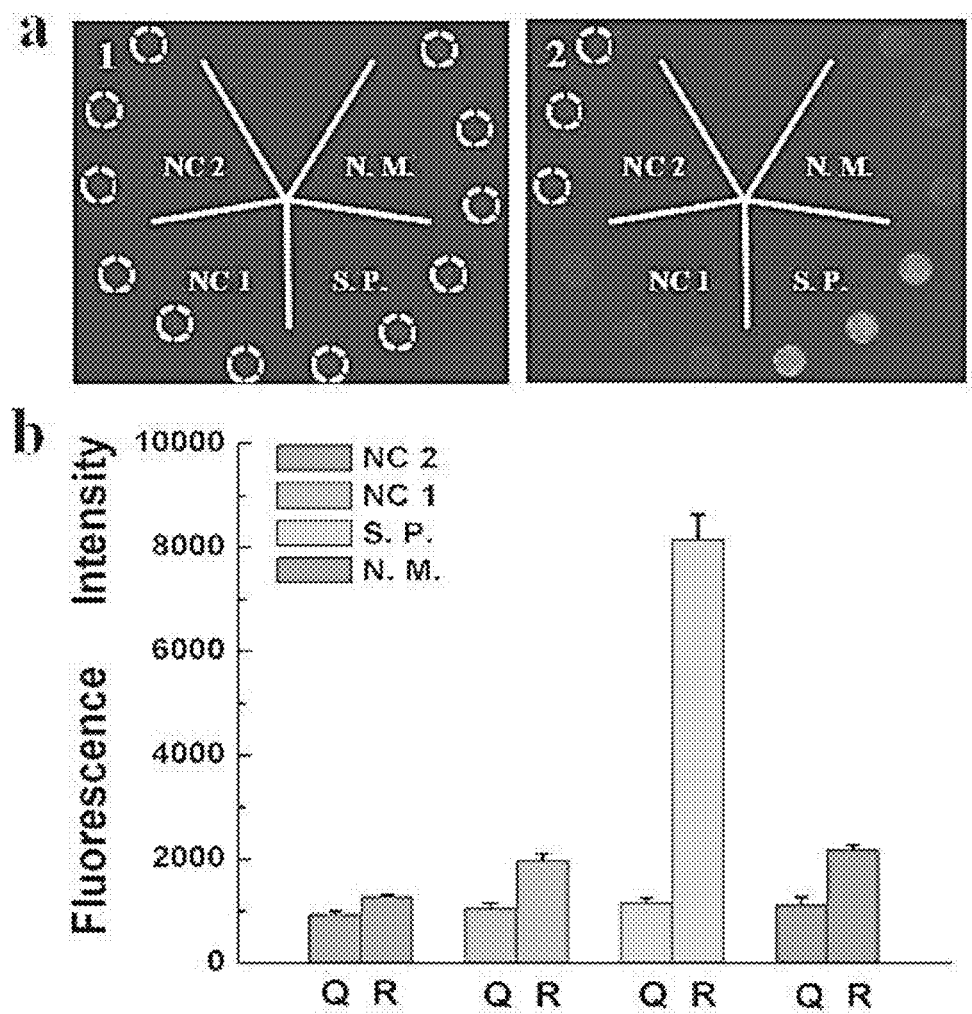
FIG. 13A-13B. Specificity detection by testing a *S. pneumoniae* DNA sample with its corresponding and non-corresponding probes. (a) Microscope images of nano-biosensors after quenching (a-1) and after recovery (a-2) with amplified *S. pneumoniae* DNA sample. (b) Fluorescence intensities of nano-biosensors after quenching (Q) and after recovery (R) with amplified *S. pneumoniae* DNA sample. Specific probe for *N. meningitidis*, *S. pneumoniae* and NC1 were first immobilized in LAMP detection zones. (*S. pneumoniae* LAMP products: 700 ng/µL).

Specificity detection was performed by testing *N. meningitidis* and *S. pneumoniae* LAMP products with their corresponding and non-corresponding probes. Specific probes for *N. meningitidis, S. pneumonia*, and NC1 with optimized concentration (1.0 μM) were pre-immobilized in LAMP detection zones. Then *N. meningitidis* DNA samples and *S. pneumoniae* DNA samples were introduced separately for LAMP reaction and detection. As shown in FIG. 12 and FIG. 13, only the target DNA sample with its corresponding probe generated bright fluorescence. The recovered fluorescence intensity of *N. meningitidis* and *S. pneumoniae* target DNA samples with their corresponding probes was more than 4.30 and 3.75 folds higher than that with their non-corresponding probes respectively, which indicating high specificity.

GO Nanosensors-Based Multiplexed Quantitative Analysis of Amplified DNA.

Figure 14:
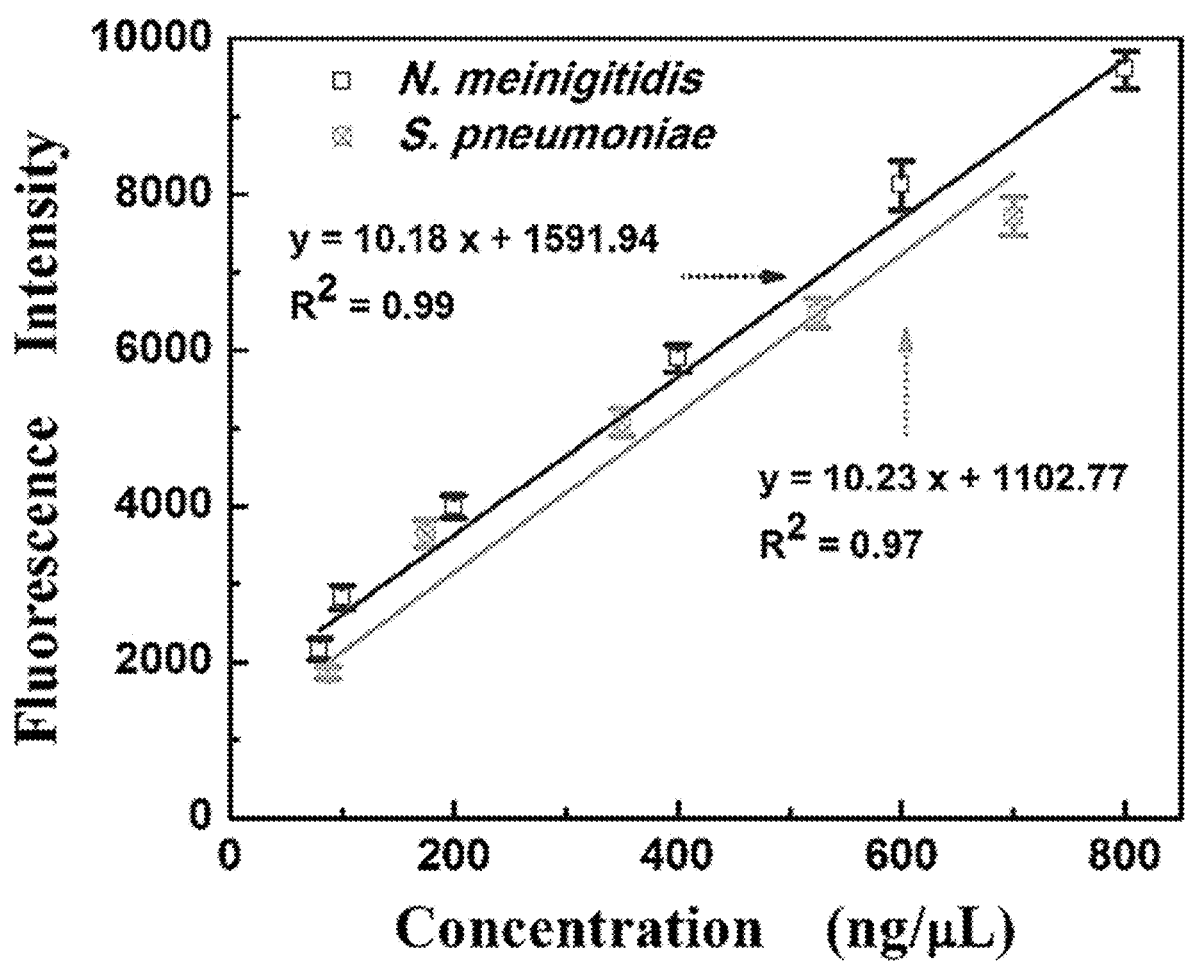
FIG. 14. GO nanosensor-based multiplexed quantitative analysis, with $R^2$ for *N. meningtidis* and *S. pneumoniae* of 0.99 and 0.97, respectively.

By using a series of diluted *N. meingitidis* and *S. pneumoniae* LAMP products, we first demonstrated the feasibility of GO nano-biosensors for multiplexed quantitative analysis, as shown in FIG. 14. The detectable LAMP product concentrations of *N. meingitidis* and *S. pneumoniae* range from 80-800 ng/μL and 87.5-700 ng/μL, respectively. This offers a simpler but more quantitative solution for multiplex LAMP analysis than conventional gel electrophoresis.

Multiplexed Quantitative Pathogen Analysis Based on Integrated LAMP and GO Nanosensors.

Figure 15:
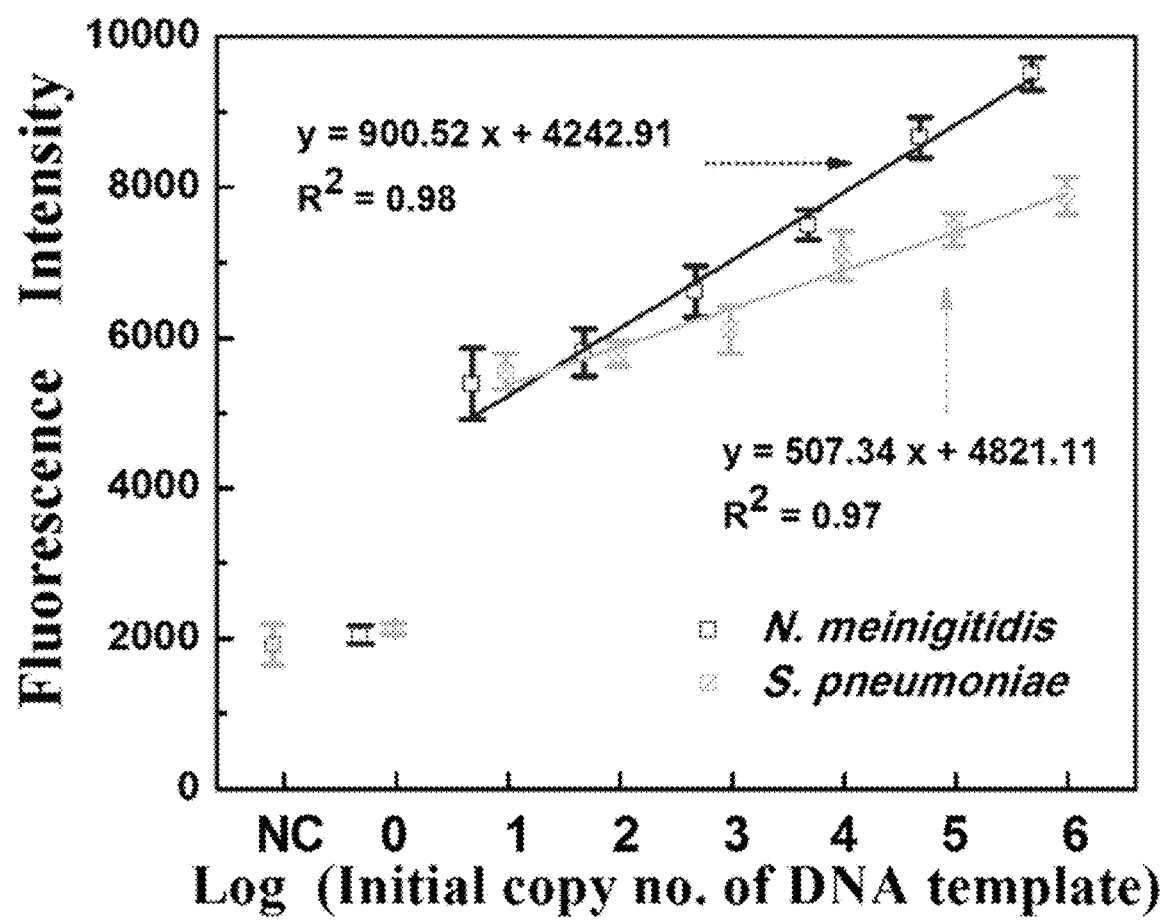
FIG. 15. Calibration curves of the fluorescence intensity after recovery versus the target LAMP products concentration of *N. meningitidis* and *S. pneumoniae*, with $R^2$ of 0.98 and 0.97, respectively.

By testing a serial of 10-fold diluted initial DNA template samples using our integrated LAMP and GO nanosensors, we performed quantitative analysis and investigated the limit of detection for *N. meningitidis* and *S. pneumoniae*. The recovered fluorescence intensities corresponding to various concentrations of initial DNA template samples were recorded to generate a calibration curve, as shown in FIG. 15. It can be seen that there was a linear relationship between the fluorescence intensity after recovery and logarithm of initial copy numbers of the DNA template in the rage of $6\text{-}6\times10^5$ copies/reaction and $12\text{-}1.2\times10^6$ copies/reaction for *N. meningitidis* and *S. pneumoniae* respectively. Quantitative analysis can help reveal the infection seriousness. On the basis of the 3-fold standard deviations of the mean fluorescent intensity of the negative control, the limit of detection (LOD) for *N. meningitidis* and *S. pneumoniae* was as low as 6 copies/reaction and 12 copies/reaction, respectively.

The invention claimed is:

1. A paper-polymer hybrid microfluidic device comprising:

(a) a microfluidic support having at least two separate layers, (i) a top layer having at least one microchannel formed in the top layer, the at least one microchannel comprises an inlet reservoir, and an outlet connected by a conduit, wherein the top layer comprises a polymer;

(ii) a bottom layer position below the top layer and bonded to the top layer and the bottom layer forming a cylindrical detection microwell, the detection microwell having an open top part in fluid communication with the at least one microchannel of the top layer, a closed bottom part positioned 1 millimeters (mm) to 4 mm below the top layer, and a horizontal cross-sectional diameter 0.5 mm to 3 mm, wherein the bottom layer comprises a polymer;

(b) a paper insert nanosensor positioned on the closed bottom part of the cylindrical detection microwell forming a floor of the microwell, the paper insert nanosensor having an adsorbed nanosensor complex comprising a fluorescently labeled aptamer probe reversibly complexed with a fluorescence quenching moiety selected from the group consisting of graphene oxide, graphene, and carbon nanoparticles, wherein the paper insert has a thickness of between 0.05 mm to 2 mm and a pore diameter of between 5 micrometers (μm) to 15 μm, and wherein the bottom layer is thicker than the paper insert; and (c) a support layer positioned below the closed bottom part of the cylindrical detection microwell forming a floor of the cylindrical detection microwell of the second layer.

2. The paper-polymer hybrid microfluidic device of claim 1, wherein the paper-polymer hybrid microfluidic device comprises a plurality of cylindrical detection microwells.

3. The paper-polymer hybrid microfluidic device of claim 2, wherein the plurality of cylindrical detection microwells are arrange in an array.

4. The paper-polymer hybrid microfluidic device of claim 1, wherein the polymer of the top layer is polydimethylsiloxane (PDMS).

5. The paper-polymer hybrid microfluidic device of claim 1, wherein the polymer of the bottom layer is polydimethylsiloxane (PDMS).

6. The paper-polymer hybrid microfluidic device of claim 1, wherein the support layer is glass, or PDMS.

7. The paper-polymer hybrid microfluidic device of claim 1, wherein the paper is porous chromatography paper.

8. The paper-polymer hybrid microfluidic device of claim 1, wherein the fluorescently labeled aptamer probe is bound to a pathogen.

9. The paper-polymer hybrid microfluidic device of claim 8, wherein the pathogen is a bacteria or virus.

10. The paper-polymer hybrid microfluidic device of claim 1, wherein the paper insert nanosensor comprises two or more distinct fluorescently labeled aptamer probes.

11. The paper-polymer hybrid microfluidic device of claim 1 wherein the bottom layer comprises two or more cylindrical detection microwells, each of the two or more cylindrical detection microwells comprising a distinct paper insert nanosensor.

* * * * *